United States Patent [19]
Lakowicz et al.

[11] Patent Number: 5,624,847
[45] Date of Patent: Apr. 29, 1997

[54] METHOD FOR OPTICALLY MEASURING CHEMICAL ANALYTES

[75] Inventors: Joseph R. Lakowicz, 10037 Fox Den Rd., Ellicott City, Md. 21042; Henryk Szmacinski, Baltimore, Md.

[73] Assignee: Joseph R. Lakowicz, Ellicott City, Md.

[21] Appl. No.: 102,806

[22] Filed: Aug. 6, 1993

Related U.S. Application Data

[63] Continuation-in-part of Ser. No. 694,282, May 3, 1991, abandoned.

[51] Int. Cl.$^6$ .................................................. G01N 21/80
[52] U.S. Cl. ..................... 436/68; 436/74; 436/163; 436/172; 128/633
[58] Field of Search ..................... 436/68, 138, 133, 436/163, 166, 172, 74; 128/633, 634

[56] References Cited

U.S. PATENT DOCUMENTS

| | | | |
|---|---|---|---|
| 4,923,819 | 5/1990 | Fernandez et al. | 436/518 |
| 4,925,804 | 5/1990 | Hale et al. | 436/501 |
| 5,196,709 | 3/1993 | Berndt et al. | 250/458.1 |
| 5,308,581 | 5/1994 | Lippitsch et al. | 422/82.08 |

OTHER PUBLICATIONS

Miyoshi et al., "A New Method of Determining Intracellular Free Ca2+ Concentration Using Quin2–Fluorescence" Photochemistry and Photobiology, vol. 53, pp. 415–418 (1991).

"Bioprobes", Molecular Probes, Inc., pp. 1–16 (1988).

Gehrich, J.L. et al., IEEE Transactions on Biomedical Engineering, vol. BME–33, No. 2 (1986) pp. 117–132.

Lippitsch, M.E. et al., Analytica Chimica Acta, vol. 205 (1988) pp. 1–6.

Lakowicz, J. et al., Applications of Fluorescence in the Biomedical Sciences (1986) pp. 29–67.

*Primary Examiner*—Jeffrey Snay
*Attorney, Agent, or Firm*—Rothwell, Figg, Ernst & Kurz

[57] ABSTRACT

A system and method in which a photoluminescent ligand is added to a sample to be analyzed in the form of a photoluminescent probe having intrinsic analyte-induced lifetime changes. The method preferably employs phase-modulation fluorometry to measure the lifetime changes. Specific probes are disclosed for measuring various analytes, particularly ionic solutes, including $H^+$, $Ca^{2+}$ and $K^+$.

18 Claims, 19 Drawing Sheets

METHOD FOR OPTICALLY MEASURING CHEMICAL ANALYTES

CROSS-REFERENCE TO RELATED APPLICATIONS

This application is a continuation-in-part of Ser. No. 07/694,282, filed on May 3, 1991, now abandoned.

FIELD OF THE INVENTION

The present invention is directed to a method for optically measuring chemical analytes and, more particularly, to a method in which a luminescent ligand is added to the sample to be analyzed in the form of a photoluminescent probe having intrinsic analyte-induced lifetime changes.

BACKGROUND OF THE INVENTION

Measurement of certain analytes in blood, such as pH and carbon dioxide, is an important aspect of the clinical care of patients. Previously, such measurements have been made using gas chromatography and other chemical methods. These methods are disadvantageous in that it is necessary to ship the blood sample to a clinical laboratory for analysis, which often results in a delay of an hour or more. Moreover, since the blood gases change rapidly, the shipping time may cause the results to be invalid. Furthermore, these known methods cannot be used for continuous in-vivo monitoring of blood.

It is known to optically measure certain analytes by using fluorescence intensity measurements. Although fluorescence intensity measurements are desirable in their simplicity, such measurements suffer from source fluctuations due to noise, drift and the like, and are subject to fluorophore bleaching, probe wash-out and background fluorescence. Further, if the media is turbid or colored, the intensity measurements will be greatly affected. Moreover, since intensity is a linear product of numerous factors, such as the amount of fluorophore in each state, the excitation intensity, the excitation and emission bandpass, the wavelength sensitivity of the detector, and the like, a complex set of calibration curves must be used to accommodate these factors.

SUMMARY OF THE INVENTION

The present invention overcomes the above difficulties by providing a method in which a luminescent ligand is added to the sample to be analyzed in the form of a photoluminescent probe having intrinsic analyte-induced lifetime changes. The lifetime measurements are advantageous over intensity measurements because they can be performed in optically dense samples or turbid media and are independent of and/or insensitive to photobleaching, probe wash-out or optical loss. The lifetime changes are measured using known time-resolved or phase-modulation fluorometry methods.

In accordance with the method of the invention, the probe can be either fluorescent, wherein the emission is from an excited singlet state to a ground state and the rate of return to the ground state occurs rapidly (on the order of 10 ns), or phosphorescent, wherein the emission is from an excited triplet state to a singlet state and the rate of return to the ground state is relatively slow (on the order of msec to sec).

The step of adding a luminescent ligand (i.e., probe) to the sample to be analyzed requires matching a particular probe to a particular analyte, so that at least a portion of the sample will be non-covalently bound to the probe so that both bound and unbound species of the probe will exist. Thus, the invention differs from prior lifetime measurement methods which rely on a collisional quenching mechanism for measuring analytes. See, for example, U.S. Pat. No. 4,810,655 to Khalil et al.; and Great Britain Patent No. 2,132,348 to Demas et al.

By definition, in collisional quenching, the probe does not bind to the analyte as required by the present invention. Instead, collisional quenching requires collisional contact between the fluorophore (probe) and the quencher (analyte). For collisional quenching to occur, the quencher must diffuse to interact with the fluorophore while the latter is in the excited state. Thus, the excited fluorophore returns to the ground state without emission of a photon.

In contrast, the present invention may have an "enhancement" of the luminescence. When the fluorescent ligand binds to the analyte, there may be an increase or decrease in intensity. It is also to be emphasized that the method of the present invention is not a Forster energy transfer mechanism, and thus is different from the method disclosed in European Patent Application 397,641 to Wolfbeis.

The method is useful for sensing the pH and carbon dioxide concentration in blood and other bodily fluids. To this end, particular probes have proven to be particularly suitable including seminaphthofluoresceins, seminaphthorhodafluors and resorufins, including those sold by MOLECULAR PROBES of Eugene, Oreg., under the tradenames SNAFL-1, Carboxy SNAFL-1, Carboxy SNAFL-2, BCECF Acid, Carboxy SNARF-1, Carboxy SNARF-2, Carboxy SNARF-6 and Carboxy SNARF-X, and resorufin derivatives such as the sodium salt and the acetate.

The method of the invention is useful in either in vitro or in vivo applications, including, for example, blood gas catheters, including optical fibers, and other bedside monitors, and non-invasive blood gas measurements. Also, the invention may be used for pH and carbon dioxide sensors for fermentors and incubators.

The method of the invention is not limited to the sensing of pH, but may also be used to sense a wide variety of other ionic solutes. For example, the calcium ion concentration of a sample may be determined by the method of the present invention. Sensing the calcium ion concentration of a sample is particularly useful for flow cytometry and fluorescent lifetime imaging applications. Such applications are generally disclosed in U.S. application Ser. No. 07/595,343, entitled Method and Apparatus for Performing Phase Fluorescence Lifetime Measurements in Flow Cytometry, filed Oct. 10, 1990, now abandoned, and U.S. application Ser. No. 07/645,525, entitled Method and Apparatus for Multi-Dimensional Phase Fluorescence Lifetime Imaging, filed Jan. 24, 1991, now abandoned, the contents of which are incorporated herein by reference. Of course, the method of the invention is generally applicable to flow cytometry and fluorescent lifetime imaging, and such applications are in no way limited to just calcium ion sensing.

Certain tetraacetic acid derivatives such as that sold by Molecular Probes under the tradename Quin-2 are particularly useful calcium ion probes, although it is contemplated that other probes, such as those sold under the tradenames Fura-2, Indo-1, Rhod-2 and Fluo-3 may also prove suitable. Also, the calcium ion indicators sold by Molecular Probes under the trade-names Calcium Green, Calcium Orange and Calcium Crimson may be used.

Further, the method of the invention may be used to measure potassium ion concentration. Certain potassium ion indicators including that sold by Molecular Probes under the name PBFI may be useful as potassium ion probes in the method of the invention.

It is to be noted that, although these various pH, calcium ion and potassium ion indicators are known commercially, these indicators generally heretofore have not been used for quantifying their corresponding analytes by photoluminescence lifetime measurements. Most recently, the probes Fura-2 and Quin-2 have been used to make fluorescent lifetime measurements in the presence and absence of calcium ions. See, respectively, S. M. Keating, "Nanosecond Fluorescence Microscopy of Single Cells", report of proceedings mailed May 3, 1990; and Miyoshi et al, "A New Method of Determining Intracellular Free $Ca^{2+}$ Concentration Using Quin2-Fluorescence", Photochemistry and Photobiology, Vol. 53, No 3, pp. 415–418 (1991).

DETAILED DESCRIPTION OF THE PREFERRED EMBODIMENTS

Figure 1:
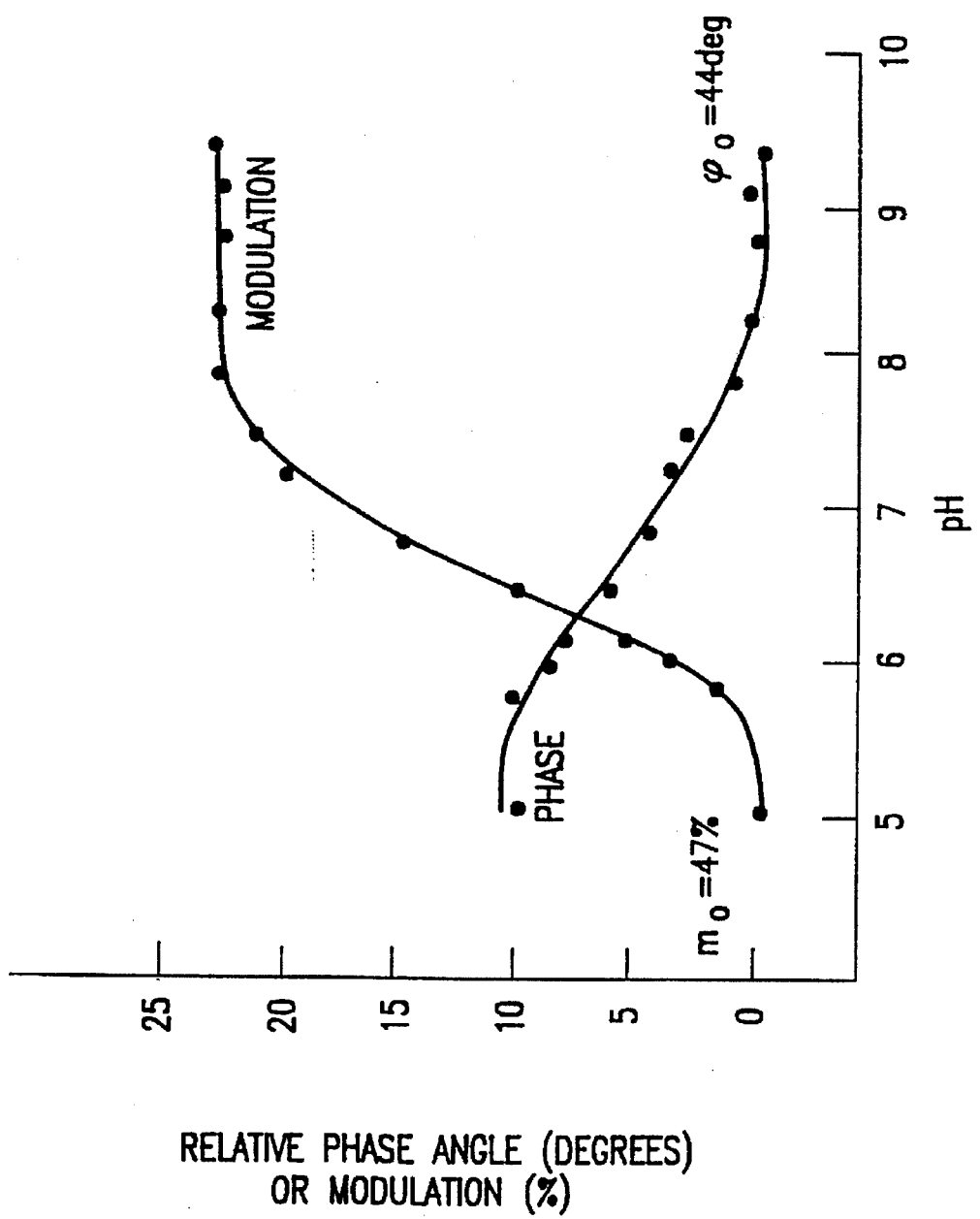
FIG. 1 is a phase/modulation versus pH graph for one of the probes, snafl-1, used in a preferred embodiment of the invention.

The method in accordance with a preferred embodiment of the invention determines and quantifies chemical analytes by changes in photoluminescence lifetimes. The method of the invention includes adding a luminescent ligand to the sample containing the analyte to be analyzed in the form of a photoluminescent probe. The probe can be either fluorescent or phosphorescent.

It is to be understood that this step requires matching a particular probe to a particular analyte, so that at least a portion of the analyte will become non-covalently bound to the probe so that both bound and unbound (i.e., free) species of the probe will then exist within the sample. The probe is chosen to have intrinsic analyte-induced lifetime changes, i.e., when the probe is bound to an analyte, the naturally occurring fluorescent or phosphorescent lifetime changes. It is to be understood that throughout this application the term "lifetime" refers to the photoluminescent lifetime defined as the inverse of the decay rate of the probe. These changes in lifetime can be measured to determine the concentration of the analyte, as will become more apparent from the discussion below.

In the context of the present invention, the term "sample" refers to compounds, surfaces, solutions, emulsions, suspensions, mixtures, cell cultures, fermentation cultures, cells, tissues, secretions and/or derivatives or extracts thereof, as well as supercritical fluids. Samples, as defined above, which can be used in the method of the present invention for sensing analytes based on fluorescence lifetimes also include samples that can be clear or turbid. Such samples to be measured according to the present invention require only that the fluorophore used be contacted with the sample such that the analyte to be sensed influences the lifetime of the fluorophore such that the lifetime varies with the presence or amount of the analyte.

Such samples can also include, e.g., animal tissues, such as blood, lymph, cerebrospinal fluid, bone marrow, gastrointestinal contents, and portions, cells or internal and external secretions of skin, heart, lung and respiratory system, liver, spleen, kidney, pancreas, gall bladder, gastrointestinal tract, smooth, skeletal or cardiac muscle, circulatory system, reproductive organs, auditory system, the autonomic and central nervous system, and extracts or cell cultures thereof. Such samples can be measured using methods of the present invention in vitro, in vivo and in situ.

Such samples can also include environmental samples such as earth, air or water samples, as well as industrial or commercial samples as compounds, surfaces, aqueous chemical solutions, emulsions, suspensions or mixtures.

Additionally, samples that can be used in the method of the present invention include cell culture and fermentation media used for growth of prokaryotic or eukaryotic cells and/or tissues, such as bacteria, yeast, mammalian cells, plant cells and insect cells.

The term "analyte" in the context of the present invention refers to elements, ions, compounds, or salts, dissociation products, polymers, aggregates or derivatives thereof. Examples of analytes that can be measured in the method of the present invention include, e.g., $H^+$, $Ca^{2+}$, $K^+$ or other compounds containing these ionic solutes, including salts, derivatives, polymers, dissociation products, or aggregates thereof.

The method of the invention further includes exciting the tagged sample with radiation from any suitable radiation source, such as a laser, an light emitting diode or the like. Light sources suitable for use in the methods of the present invention, also include noble gas light sources such as helium, neon, argon, krypton, xenon, and radon, and combinations, thereof. Light sources can include gas lamps or lasers which provide uniform light that has been filtered, polarized, or provided as a laser source, such as a coherent wave (CW) laser or a pulsed laser. Specified impurities can be added to the above described noble gas light sources to provide suitable light sources for use in the present invention with varying wavelengths such as emission and excitation wavelengths. Such impurities include Group II metals, such as zinc, cadmium, mercury, strontium, selenium and ruthenium. A green helium-neon laser is particularly preferred in the present invention because it is inexpensive and reliable.

In a preferred embodiment, the intensity of the excitation radiation is modulated at a particular modulation frequency and the lifetime determined using known phase-modulation, i.e., frequency-domain, techniques. Alternatively, a pulsed radiation source may be used and the lifetime of the sample determined using known time-resolved methods. Both phase-modulation and time-resolved fluorometry methods are well known in the prior art, see Lakowicz, *Principles of Fluorescence Spectroscopy*, Plenum Press, 1983, Chapter 3. However, current instrumentation renders the phase-modulation method more expedient. For the sake of conciseness, only the phase-modulation method will be discussed further herein, but it is understood that these same principles generally apply to time-resolved measurements.

When the sample is excited with radiation whose intensity is modulated, for example, in a sinusoidal manner, the time lag between absorption and emission causes the emission to be delayed in phase and demodulated relative to the excitation radiation. As discussed above, when a luminescent ligand is added to the sample, at least a portion of the analyte will bind with the ligand, i.e., probe, so that both bound and unbound species of the probe will now exist within the sample. The probe is chosen so that there will be a significant difference in the luminescent lifetime between the bound and unbound species. The phase shift and the corresponding demodulation factor m can be measured and used to calculate the photoluminescent lifetime based on well known formulae. See, Lakowicz, supra. It is desirable to select the modulation frequency in a range that coincides with the frequency at which the differences between the measured phase angles and the demodulations of the bound and unbound ligand are maximal.

Thus, according to the method of the invention, the emission radiation is detected, the phase shift (in degrees) and the demodulation factor m (as a percentage change) are measured, and the apparent photoluminescent lifetime may be calculated therefrom. An absolute value of difference in phase angle between the bound and free forms of the ligand of the order of 30–60 degrees at some preselected frequency, and a difference in modulation factor on the order of 30–87%, are preferred, which is shown in the examples below. These ranges of phase angles and modulation factors are preferred because they offer the greatest precision and dynamic range.

The absolute values of the frequency-dependent phase differences and demodulations are determined by the photoluminescent lifetimes of the free and bound ligand. In addition, if the excitation and emission spectra are not congruent, the effects depicted in FIG. 16 can occur, whereby at particular wavelengths of excitation or emission one form or the other of the probe is preferentially excited or its emission preferentially observed. In such cases, the apparent analyte concentration (for pH, the apparent pKa) varies with excitation or emission wavelength. This is advantageous, in that the method of the present invention allows the range of concentrations that can be accurately measured with a single probe to be easily varied by selection of the appropriate excitation and/or emission wavelengths.

Figure 15:
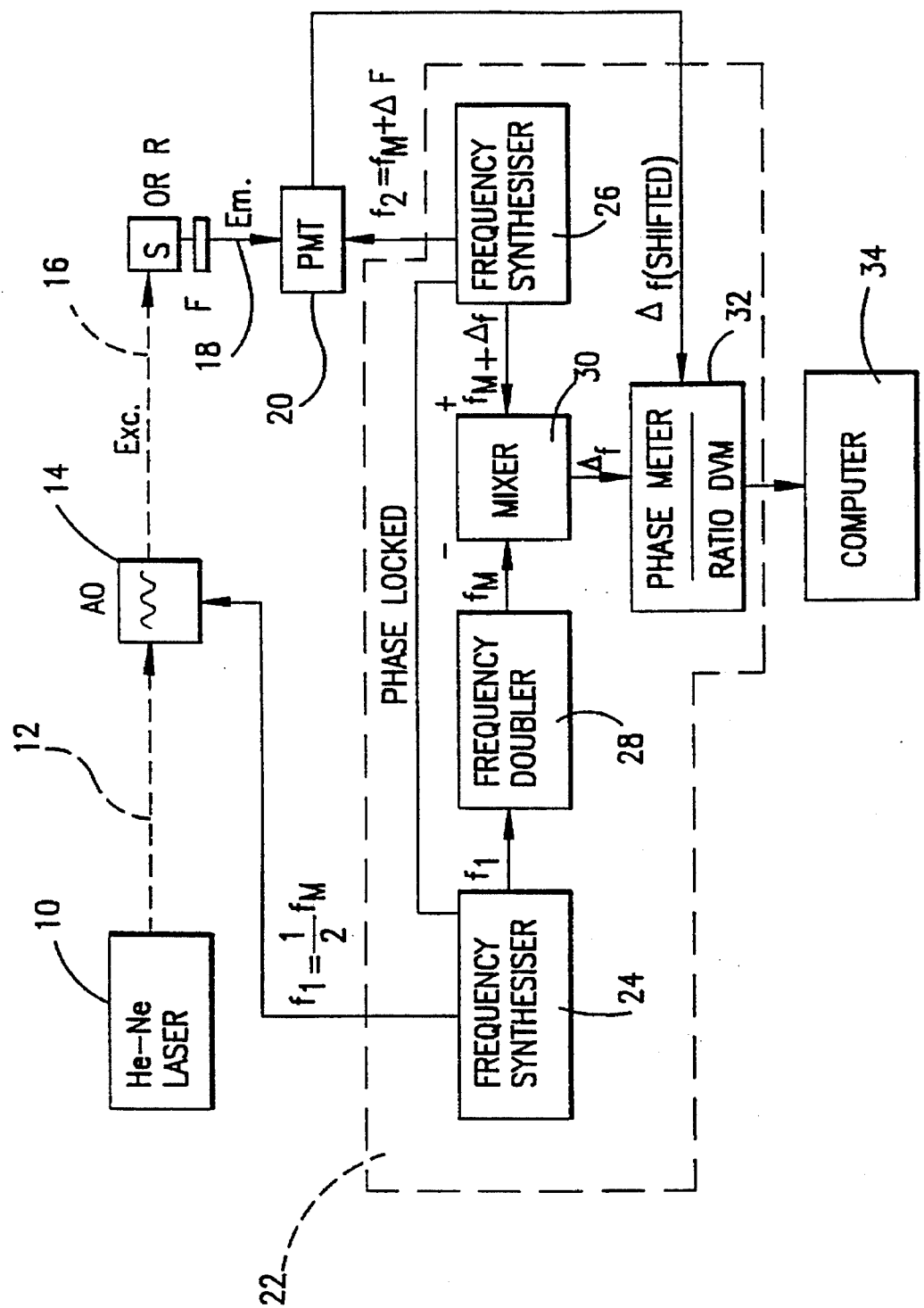
FIG. 15 is a schematic diagram showing an embodiment of the preferred instrumentation for use in the present invention.

One preferred embodiment of the instrumentation for use with the method of the invention is schematically shown in FIG. 15. It is to be understood, however, that any suitable instrumentation can be used, including, for example, those disclosed in U.S. Pat. No. 4,937,457 to Mitchell, and those disclosed in Lakowicz, "A Review of Photon-Counting and Phase-Modulation Measurements of Fluorescence Decay Kinetics", *Applications of Fluorescence in the Biomedical Sciences*, pp. 29–67 (1986), the contents of which are incorporated herein by reference.

As shown in FIG. 15, radiation source 10, in this case a helium-neon laser having an emission of 543 nm, emits excitation beam 12 which is modulated by acoustooptic modulator 14 at a frequency f1 to create sinusoidally-modulated excitation beam 16. It is to be understood that modulator 14 need not be an acoustooptic modulator, but that any suitable modulator may be used, such as an electrooptic modulator. Moreover, the modulation need not be sinusoidal, but of any desired shape. Also, the modulator need not be external, but instead the light source may be intrinsically modulated.

Sinusoidally-modulated excitation beam 16 irradiates sample S, which contains the analyte to be measured and the appropriate probe, with both bound and unbound species of the probe being contained within the sample. The irradiated sample emits emitted beam 18 which is detected at photomultiplier tube 20. Emitted beam 18 is amplitude modulated at the same frequency as the excitation but it is phase shifted and demodulated with respect to the excitation. It may be desirable to filter emitted beam 20 with optical filter F in order to change the effective sensitivity range of the detector, as explained above. Typically, filter F is a 2-73 Corning filter, but any desired filter may be used, such as a Corning 3-67 filter.

Cross-correlation circuit 22 includes first frequency synthesizer 24 which generates frequency f1, equal to one-half of a modulation frequency fM to drive acoustooptic modulator 14, and the PMT dynode chain. Cross-correlation circuit 22 also includes second frequency synthesizer 26 which generates a frequency f2 equal to the modulation frequency fM plus a cross-correlation frequency $\Delta f$ to drive photomultiplier tube 20. First frequency synthesizer 24 is coupled to frequency doubler 28, which directs a signal having a frequency equal to the modulation frequency fM to mixer 30. Second frequency synthesizer 26 also directs a signal having frequency f2 equal to the modulation frequency fM plus the cross-correlation frequency $\Delta f$ to mixer 30. Mixer 30 produces an output signal having a frequency equal to $\Delta f$, the difference between fM and f2.

Mixer 30 and photomultiplier tube 20 are each connected to phase meter/digital voltmeter 32. Phase meter/digital voltmeter 32 compares the output signal having a frequency $\Delta f$ received from mixer 30 and the signal having a frequency $\Delta f$(shifted) received from photomultiplier tube 20 to calculate the phase shift $\phi$, and the demodulation factor m which is stored in computer 34.

A. Measuring pH and Carbon Dioxide Concentration

As discussed above, a particular probe is selected to have intrinsic photoluminescent lifetime changes induced by the particular analyte to be measured. To measure pH, for example, suitable probes include certain seminaphthorhodafluors, seminaphthofluoresceins (including BCECF acid) and resorufins. Specific example structures include:

SEMINAPHTHORHODAFLUORS

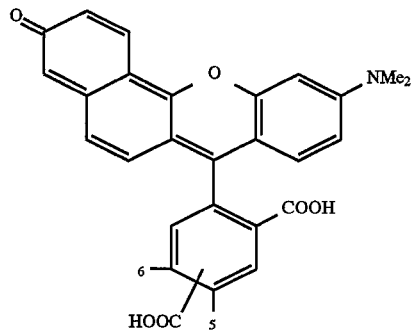

carboxy SNARF-1

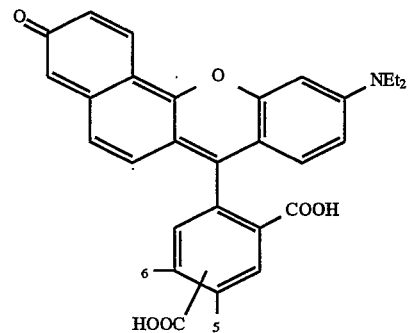

carboxy SNARF-2

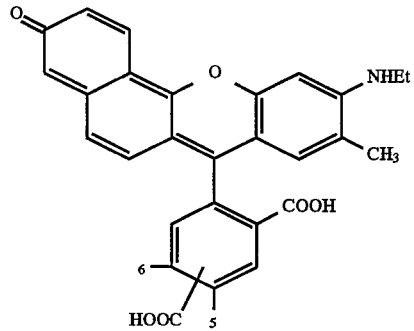

carboxy SNARF-6

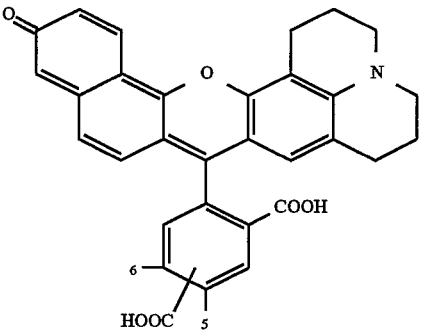

carboxy SNARF-X

SEMINAPHTHOFLUORESCEINS

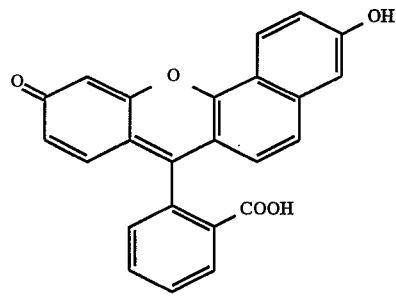

SNAFL-1

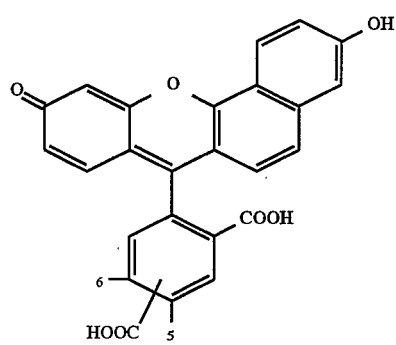

carboxy SNAFL-1

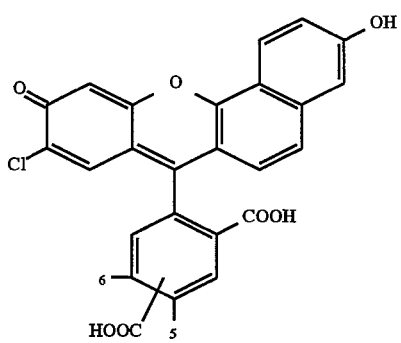

carboxy SNAFL-2

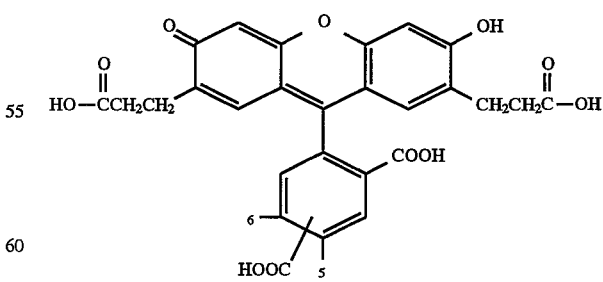

BCECF acid

-continued
RESORUFINS

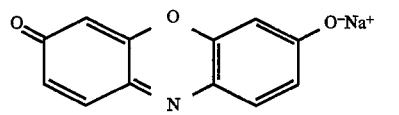

Resorufin sodium salt

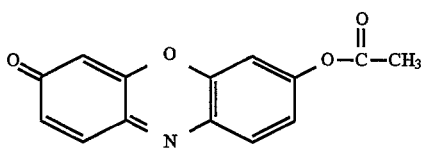

Resorufin acetate

These probes are available under the above-given tradenames from Molecular Probes, Inc., Eugene, Oregon, and are commercially sold as wavelength-shift pH indicators for intensity measurements. The seminaphthorhodafluors and seminaphthofluoresceins are disclosed in U.S. Pat. No. 4,945,171, the contents of which is incorporated herein by reference.

All of the following examples were taken in 80 mM Tris at 25 degrees C.

EXAMPLE 1

A sample containing the pH indicator Snafl-1 was irradiated using a green helium-neon laser having an excitation wavelength of 543 nm modulated at a modulation frequency of 135 MHz. A Corning 2-73 filter was used to filter the emission beam. As shown in FIG. 1, at pH 7.24, the measured phase shift with respect to the modulated excitation was 48.0 degrees, and the modulation of the emission was 66.8% of the modulation of the excitation. In FIG. 1, the phase is depicted as relative to its value at pH=9.5 of 44.0 degrees with respect to the excitation. Similarly, the modulation is depicted relative to its value at pH=5.0 of 47.0%.

EXAMPLE 2

Figure 2:
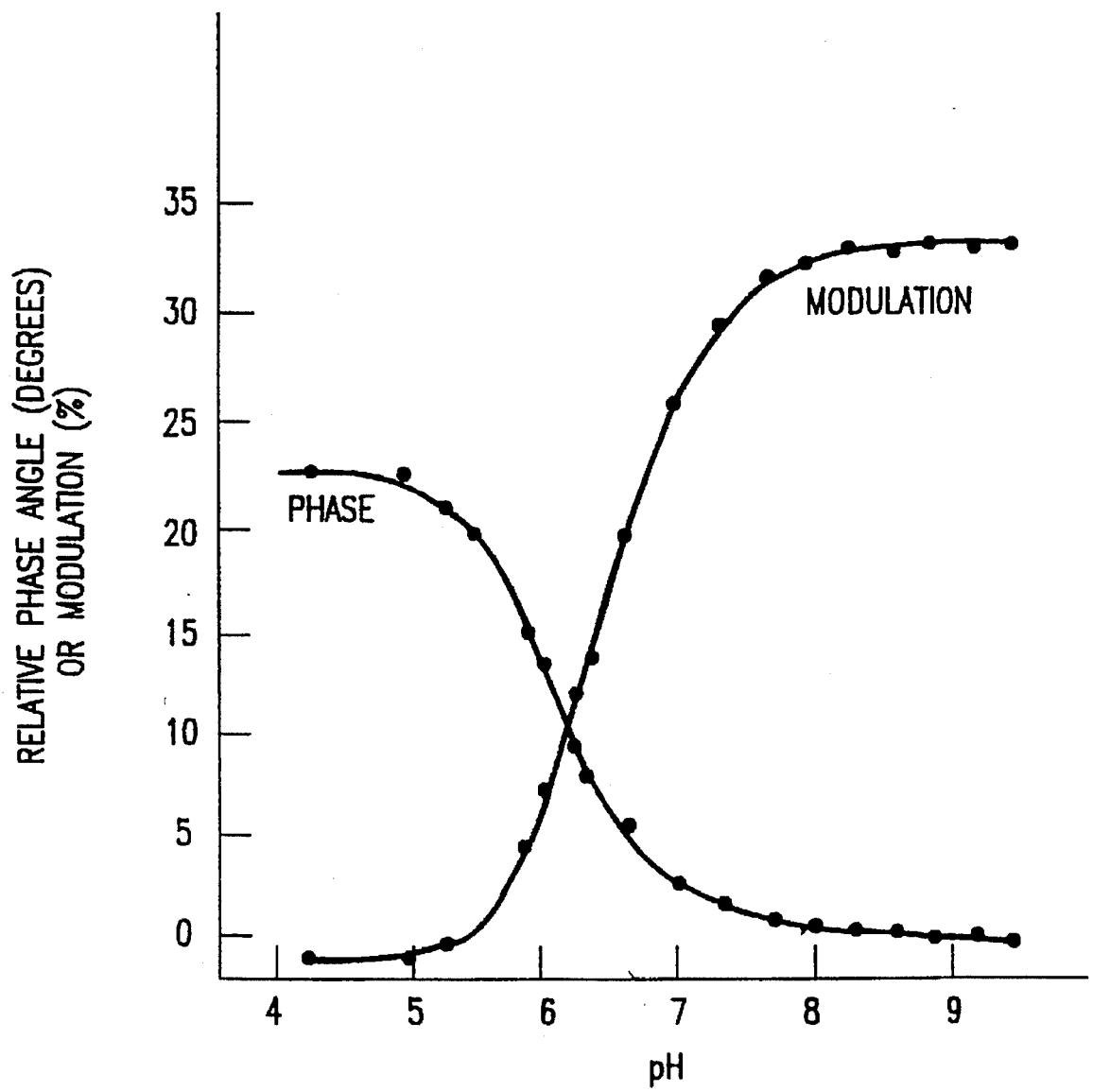
FIG. 2 is a phase/modulation versus pH graph for another of the probes, carboxy snafl-1, used in another preferred embodiment of the invention.

A sample containing the pH indicator Carboxy Snafl-1 was irradiated using a green helium-neon laser having an excitation wavelength of 543 nm modulated at a modulation frequency of 135 MHz. A Corning 2-73 filter was used to filter the emission beam. As shown in FIG. 2, at pH 7.02, the measured phase shift with respect to the modulated excitation was 46.1 degrees, and the modulation of the emission was 61.0% of the modulation of the excitation. In FIG. 2, the phase is depicted as relative to its value at pH=9.5 of 43.0 degrees with respect to the excitation. Similarly, the modulation is depicted relative to its value at pH=4.3 of 36.0%.

EXAMPLE 3

Figure 3:
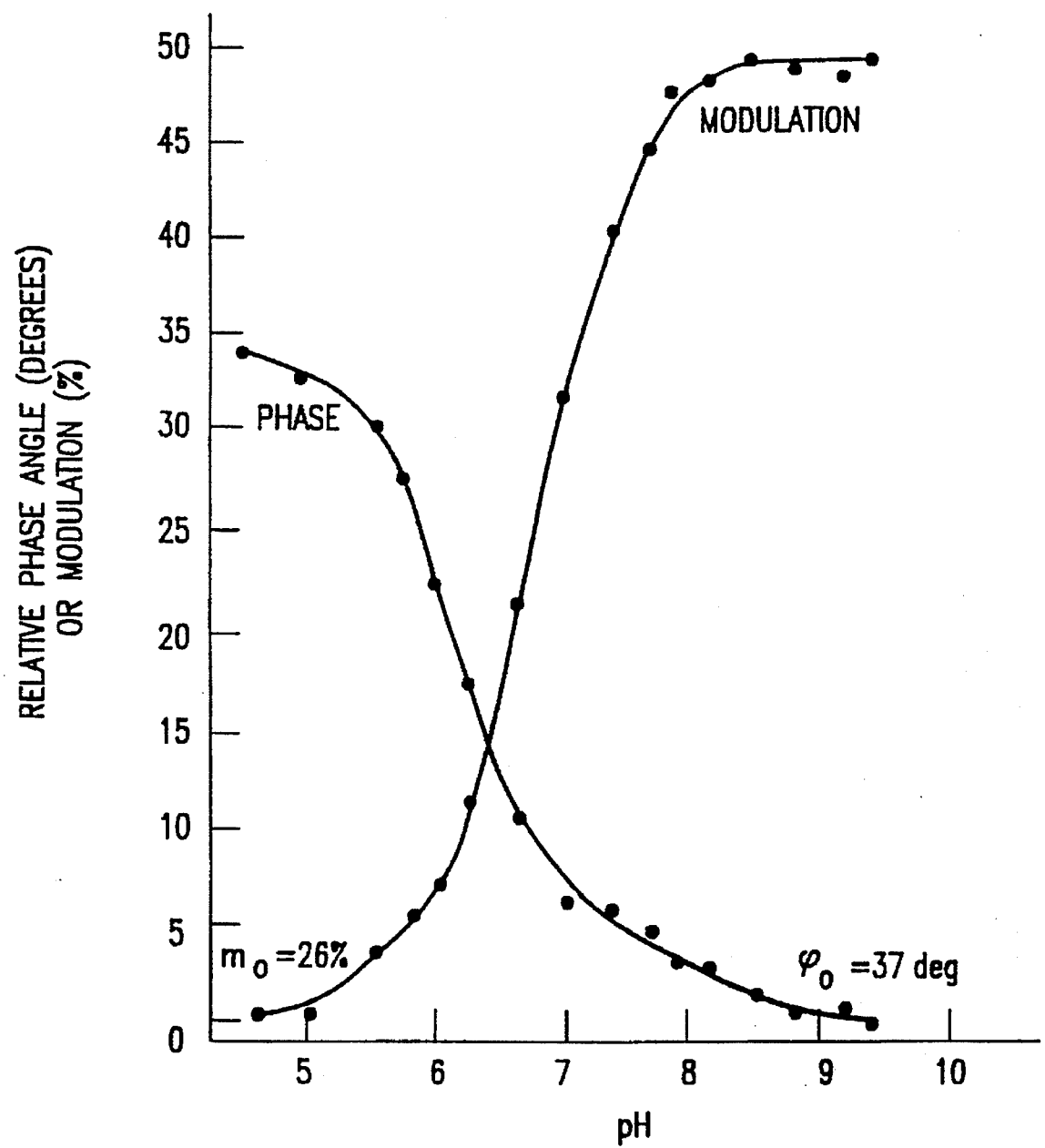
FIG. 3 is a phase/modulation versus pH graph for another of the probes, carboxy snafl-2, used in another preferred embodiment of the invention.

A sample containing the pH indicator Carboxy Snafl-2 was irradiated using a green helium-neon laser having an excitation wavelength of 543 nm modulated at a modulation frequency of 135 MHz. Initially, a Corning 2-73 filter was used to filter the emission beam. As shown in FIG. 3, at pH 7.10, the measured phase shift with respect to the modulated excitation was 43.6 degrees, and the modulation of the emission was 57.8% of the modulation of the excitation.

Figure 17:
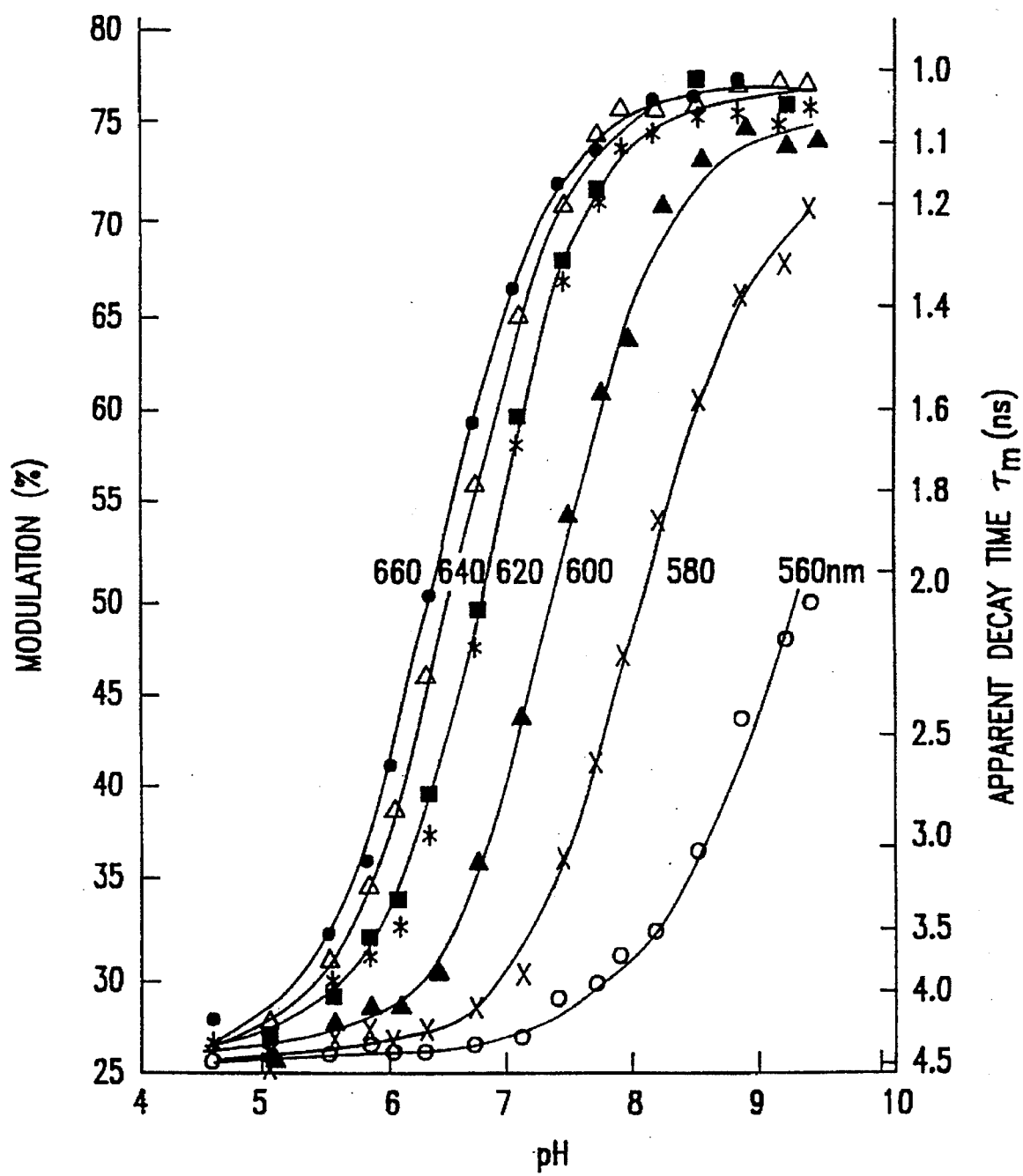
FIG. 17 is another modulation versus pH graph for the probe shown in FIG. 3.

As shown in FIG. 17, further experimentation was conducted at various emission wavelengths. At pH=7.10, the modulations with respect to the modulated excitations were 26.7% at 560 nm, 31.3% at 580 nm, 43.6% at 600nm, 59.3% at 620 nm, 64.6% at 640 nm, and 65.9% at 660 nm.

Figure 16:
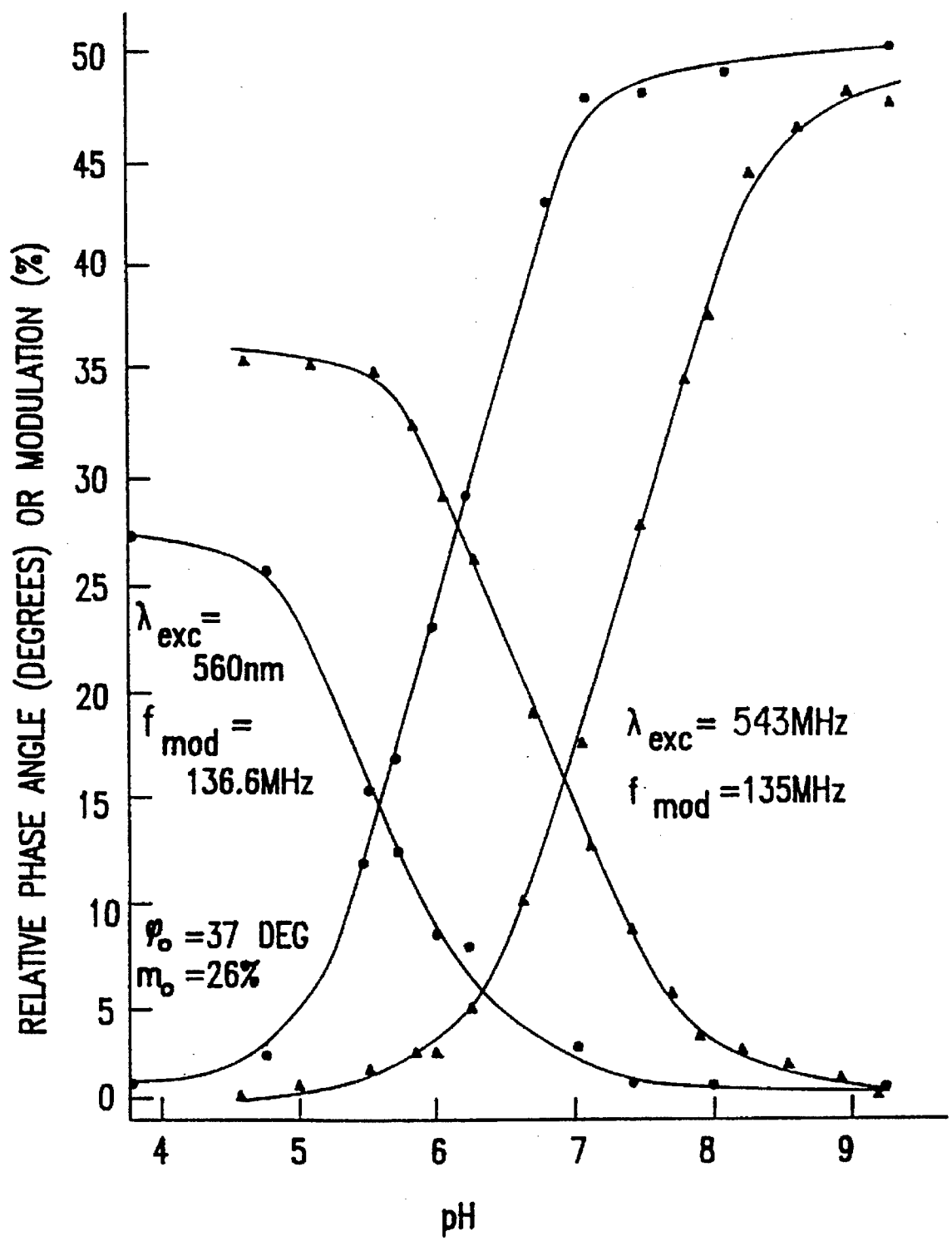
FIG. 16 is another phase/modulation versus pH graph for the probe shown in FIG. 3.

As shown in FIG. 16, it is apparent that at pH=7.0, for an excitation wavelength of 543 nm, the modulation is 43.6% with respect to the modulated excitation, whereas for an excitation wavelength of 560 nm, the modulation is 28.0%. Similarly, the phase angle at an excitation wavelength of 543 nm, is 51.0 degrees and at 560 nm, is 82.0 degrees.

As is apparent from FIGS. 3, 16 and 17, the probe carboxy SNAFL-2 can be used in the method of the present invention to accurately measure pH in the range of 5 to 9, i.e., over a concentration range of 4 decades.

EXAMPLE 4

Figure 4:
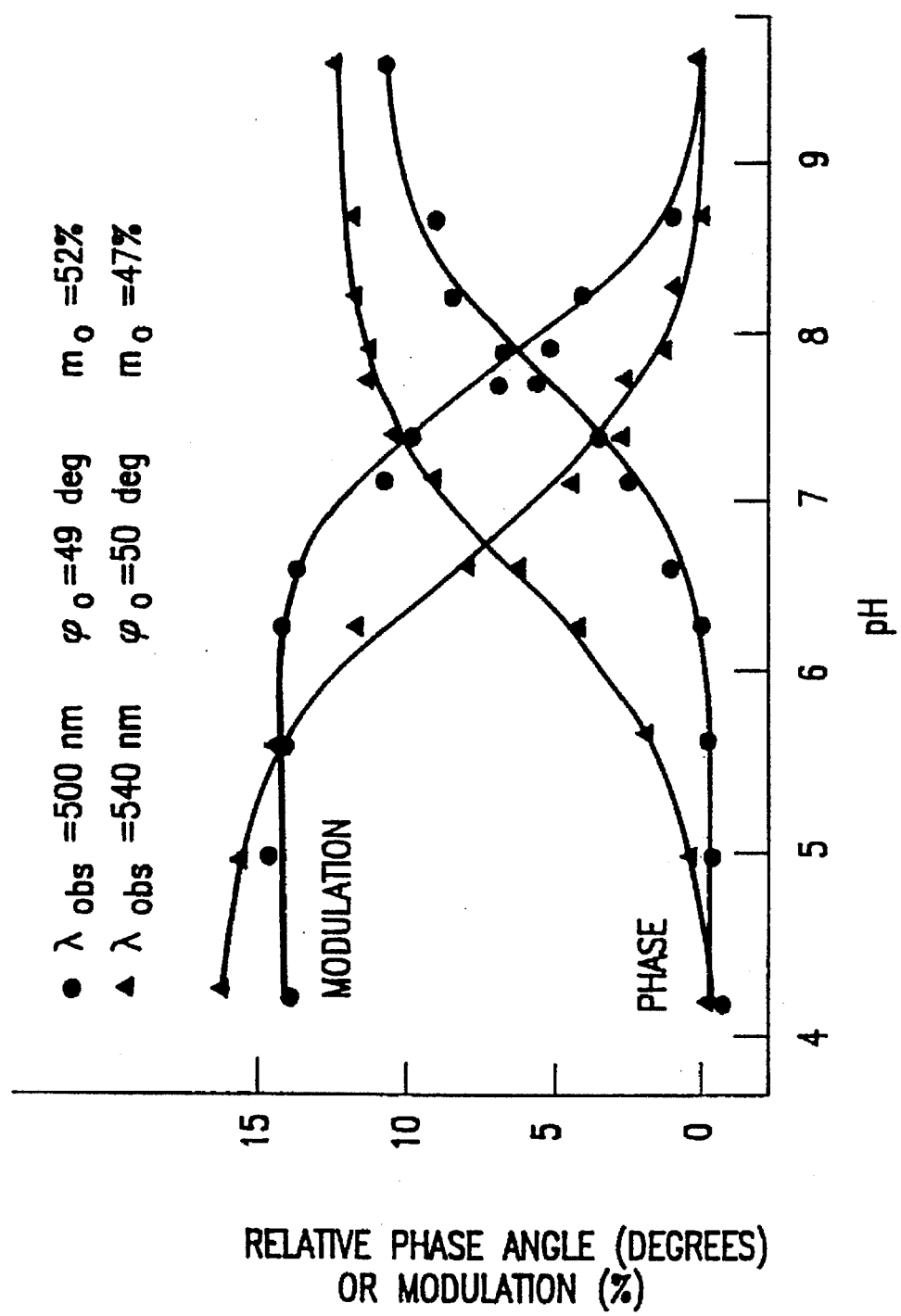
FIG. 4 is a phase/modulation versus pH graph for another of the probes, BCECF acid, used in another preferred embodiment of the invention.

A sample containing the pH indicator BCECF acid was irradiated using a helium-cadmium laser having an excitation wavelength of 500 nm modulated at a modulation frequency of 65.0 MHz. As shown in FIG. 4, at pH 7.13, the measured phase shift with respect to the modulated excitation was 51.6 degrees, and the modulation of the emission was 62.7% of the modulation of the excitation. In FIG. 4, the phase is depicted as relative to its value at pH=4.2 of 49.0 degrees with respect to the excitation. Similarly, the modulation is depicted relative to its value at pH=9.5 of 52.0%.

At an excitation wavelength of 540 nm and a pH of 7.13, the measured phase shift was 58.7 degrees and the modulation was 51.4%. Again, the phase is depicted as relative to its value at pH=4.2 of 50.0 degrees with respect to the excitation, and the modulation is depicted relative to its value at pH=9.5 of 47.0%.

EXAMPLE 5

Figure 5:
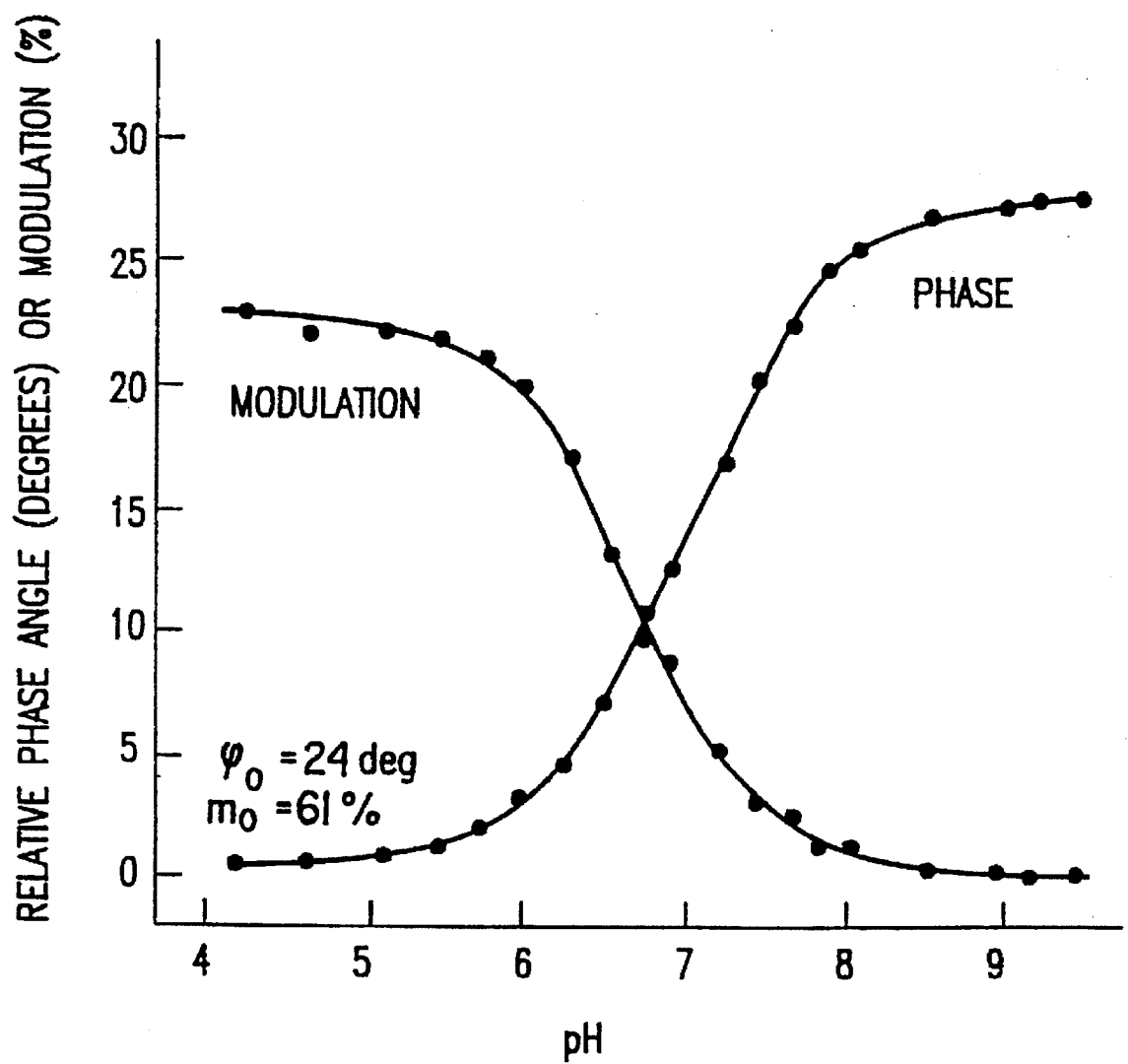
FIG. 5 is a phase/modulation versus pH graph for another of the probes, carboxy snarf-1, used in another preferred embodiment of the invention.

A sample containing the pH indicator Carboxy Snarf-1 was irradiated using a green helium-neon laser having an excitation wavelength of 543 nm modulated at a modulation frequency of 135 MHz. A Corning 2-73 was used to filter the emission beam. As shown in FIG. 5, at pH 6.91, the measured phase shift with respect to the modulated excitation was 36.5 degrees, and the modulation of the emission was 70.0% of the modulation of the excitation. The phase is depicted as relative to low pH and the modulation as relative to high pH.

Figure 12:
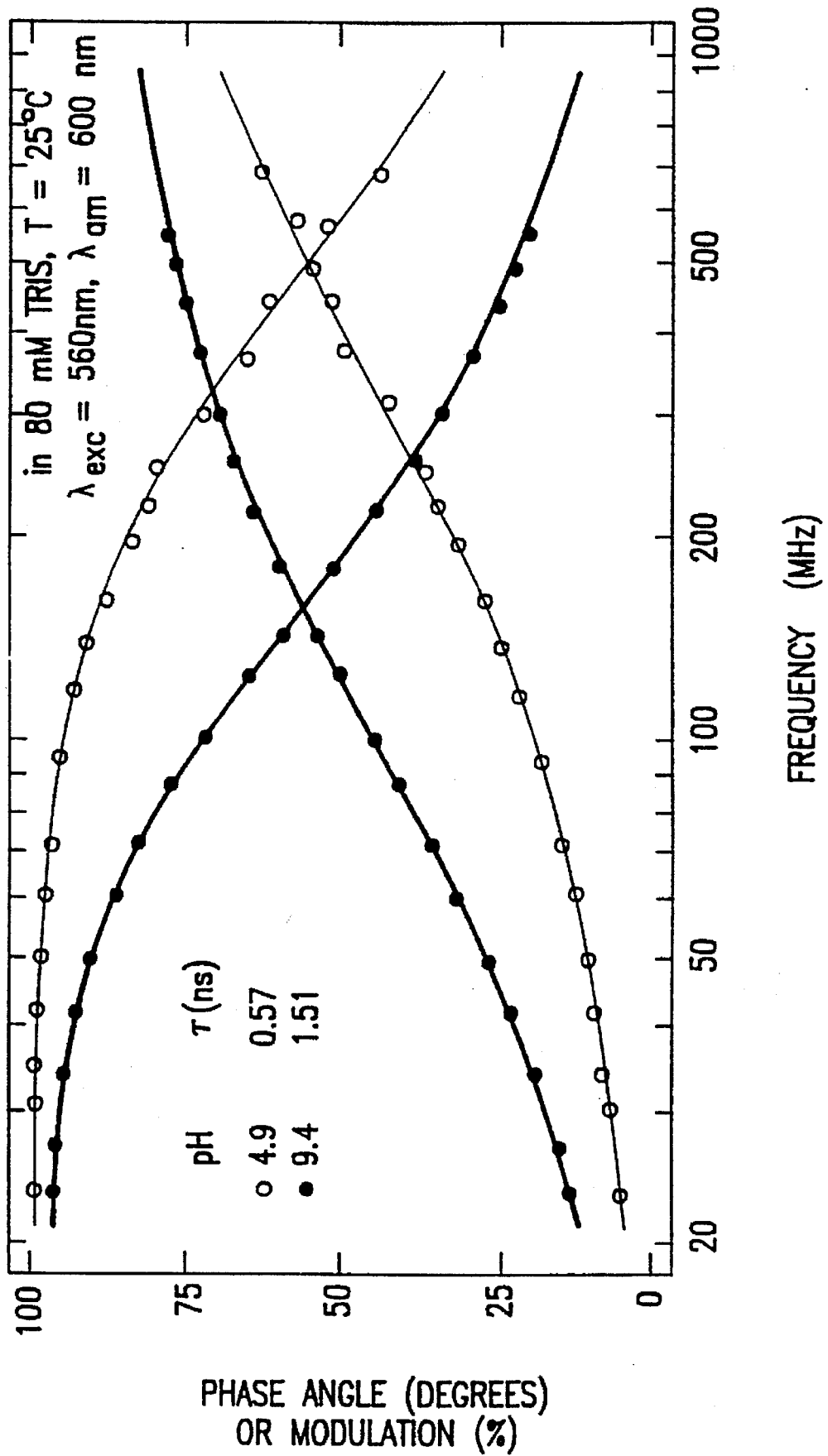
FIG. 12 is a phase/modulation versus frequency graph for the probe in FIG. 5.

As can be seen from FIG. 12, the difference in phase angles observed for this probe in the bound and unbound forms is maximal in the range of about 135 MHz; thus a modulation frequency in this range is preferred because it provides optimum precision and dynamic range.

EXAMPLE 6

Figure 6:
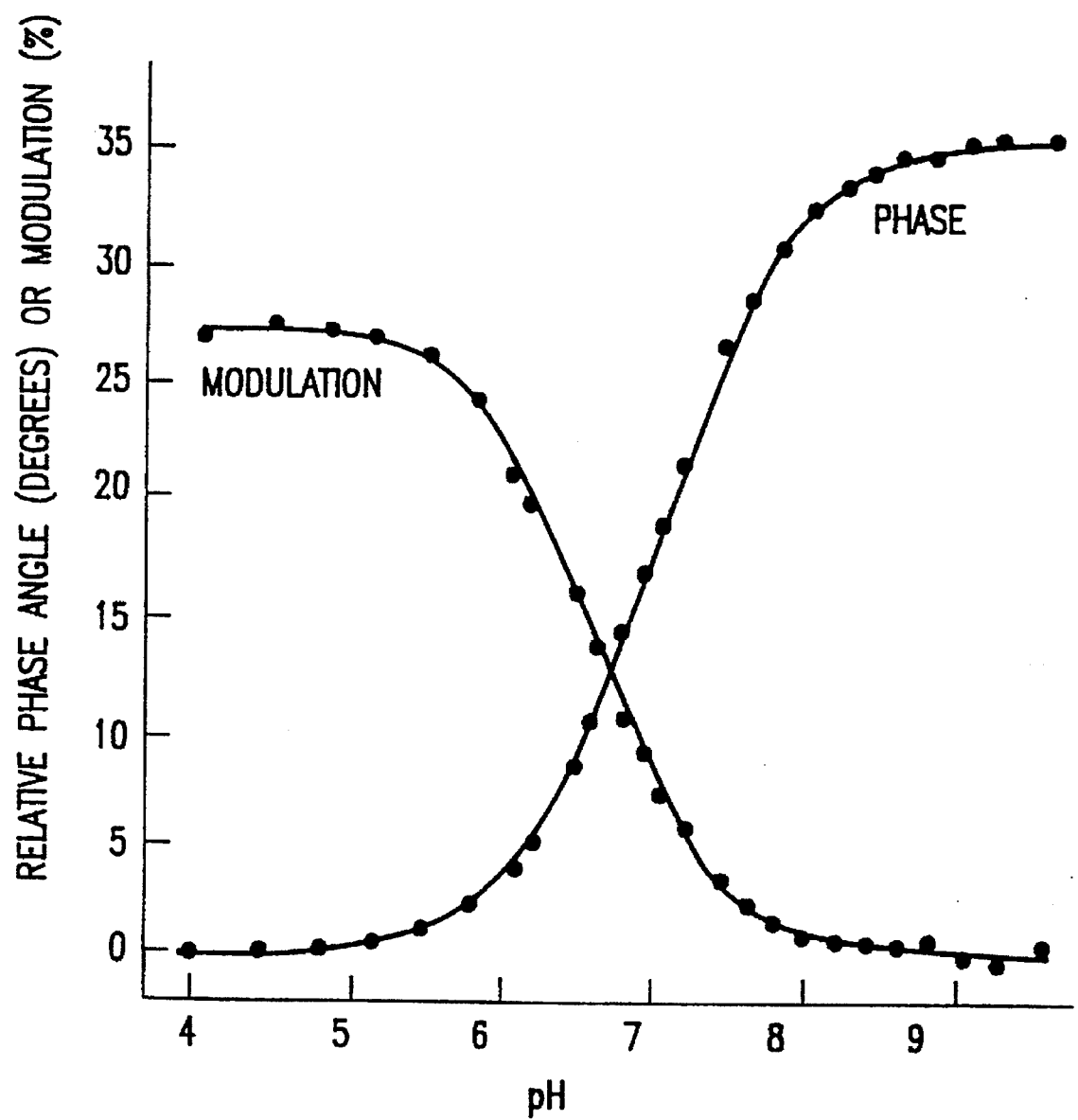
FIG. 6 is a phase/modulation versus pH graph for another of the probes, carboxy snarf-2, used in another preferred embodiment of the invention.

A sample containing the pH indicator Carboxy Snarf-2 was irradiated using a green helium-neon laser having an excitation wavelength of 543 nm modulated at a modulation frequency of 135 MHz. Initially, a Corning 2-73 filter was used to filter the emission beam. As shown in FIG. 6, at pH 7.0, the measured phase shift with respect to the modulated excitation was 27.0 degrees, and the modulation of the emission was 65.0% of the modulation of the excitation. In FIG. 6, the phase is depicted as relative to its value at pH=4.9 of 10.0 degrees with respect to the excitation. Similarly, the modulation is depicted relative to its value at pH=9.2 of 58.0%.

EXAMPLE 7

Figure 7:
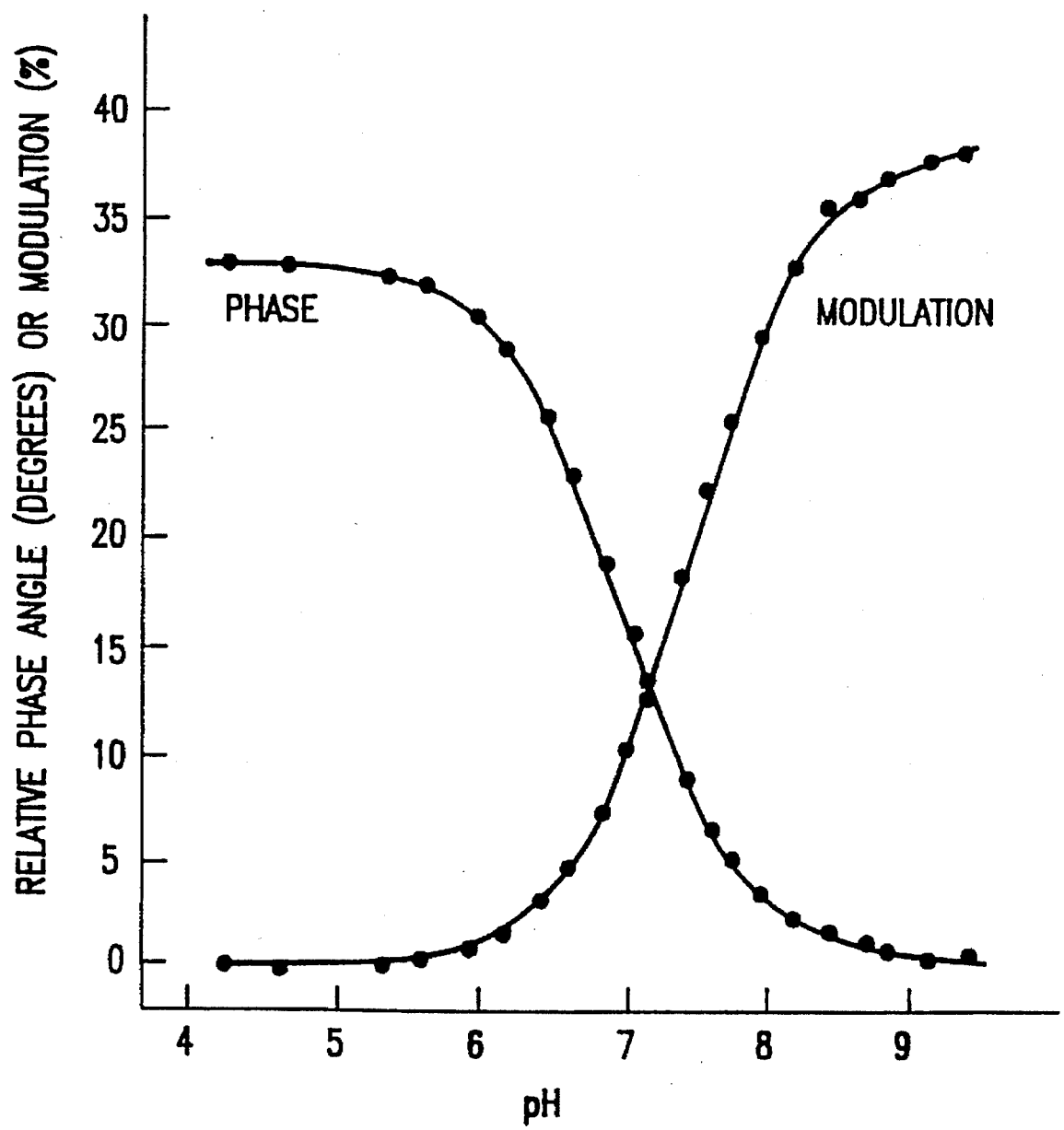
FIG. 7 is a phase/modulation versus pH graph for another of the probes, carboxy snarf-6, used in another preferred embodiment of the invention.

A sample containing the pH indicator Carboxy Snarf-6 was irradiated using a green helium-neon laser having an excitation wavelength of 543 nm modulated at a modulation frequency of 135 MHz. Initially, a Corning 2-73 filter was used to filter the emission beam. As shown in FIG. 7, at pH 6.92, the measured phase shift with respect to the modulated excitation was 59.8 degrees, and the modulation of the emission was 34.6% of the modulation of the excitation. The phase is depicted relative to its high pH value of 41.7 degrees, and the modulation is depicted relative to its low pH value of 25.3%.

EXAMPLE 8

Figure 8:
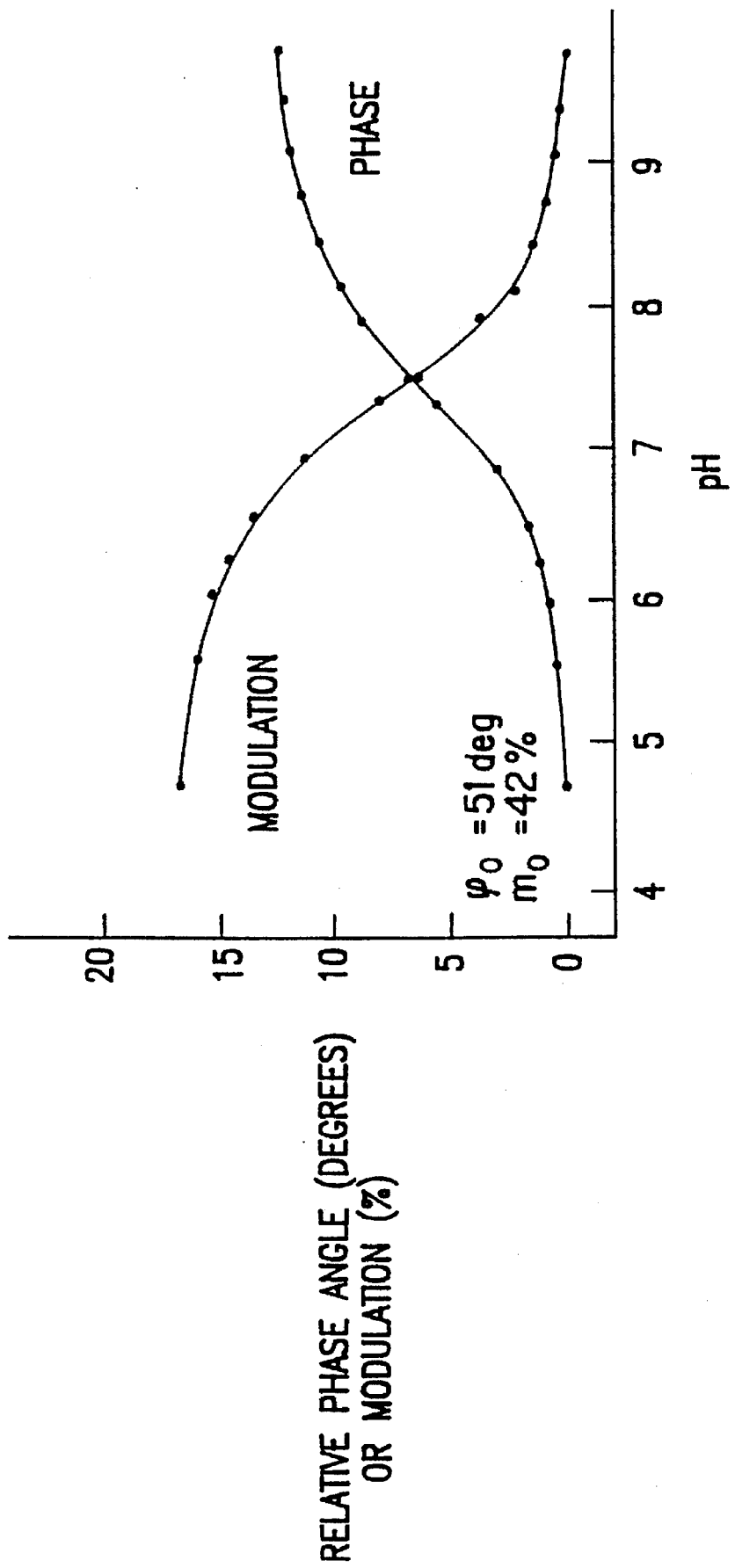
FIG. 8 is a phase/modulation versus pH graph for another of the probes, carboxy snarf-X, used in another preferred embodiment of the invention.

A sample containing the pH indicator Carboxy Snarf-X was irradiated using a green helium-neon laser having an excitation wavelength of 543 nm modulated at a modulation frequency of 135 MHz. A Corning 2-73 filter was used to filter the emission beam. As shown in FIG. 8, at pH 6.88, the measured phase shift with respect to the modulated excitation was 54.0 degrees, and the modulation of the emission was 53.6% of the modulation of the excitation. In FIG. 8, the phase is depicted as relative to its value at pH=4.8 of 51.0 degrees with respect to the excitation. Similarly, the modulation is depicted relative to its value at pH=9.5 of 42.0%.

EXAMPLE 9

Figure 9A:
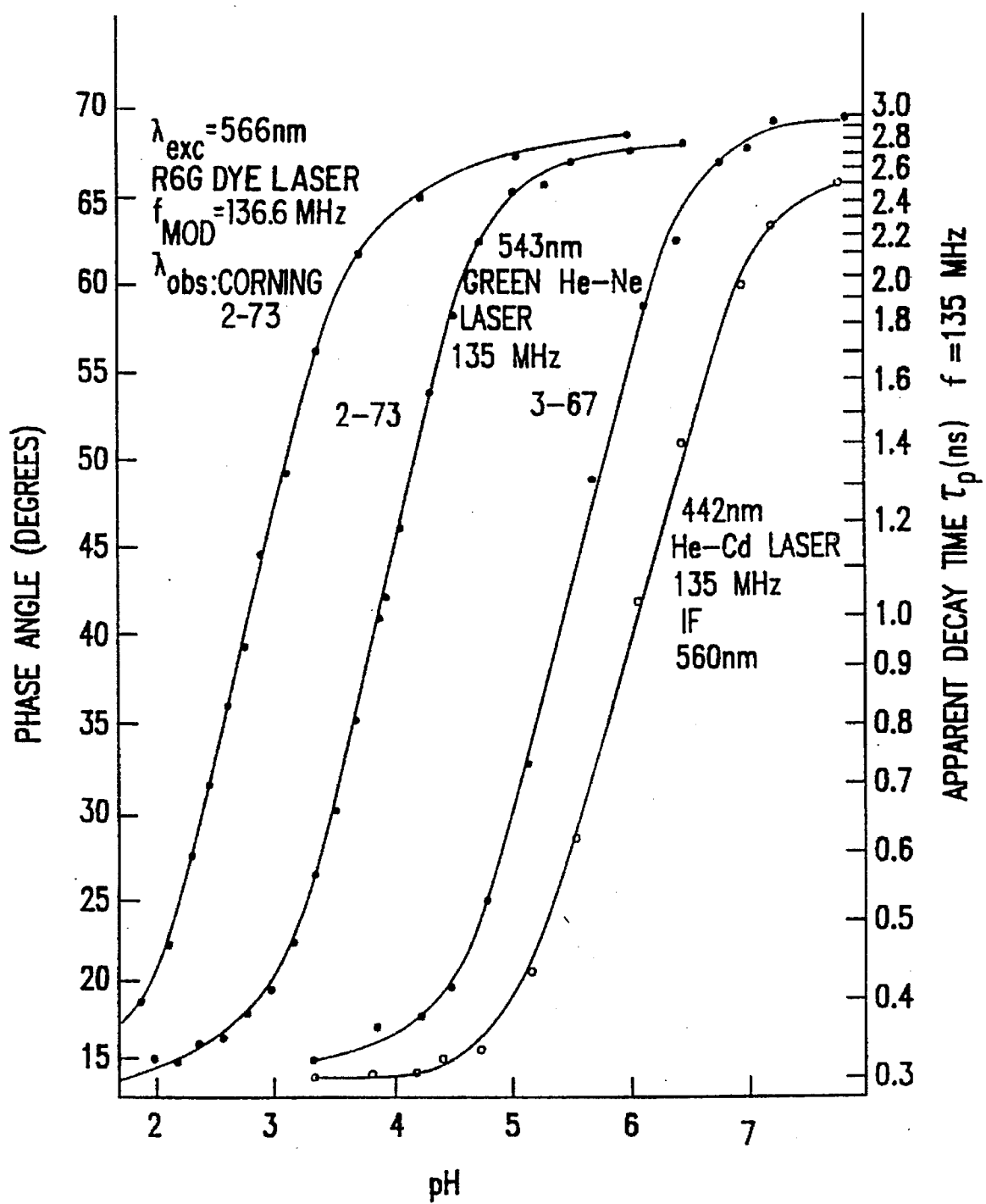
FIG. 9A is a phase versus pH graph for another of the probes, resorufin sodium salt, used in another preferred embodiment of the invention.
Figure 9B:
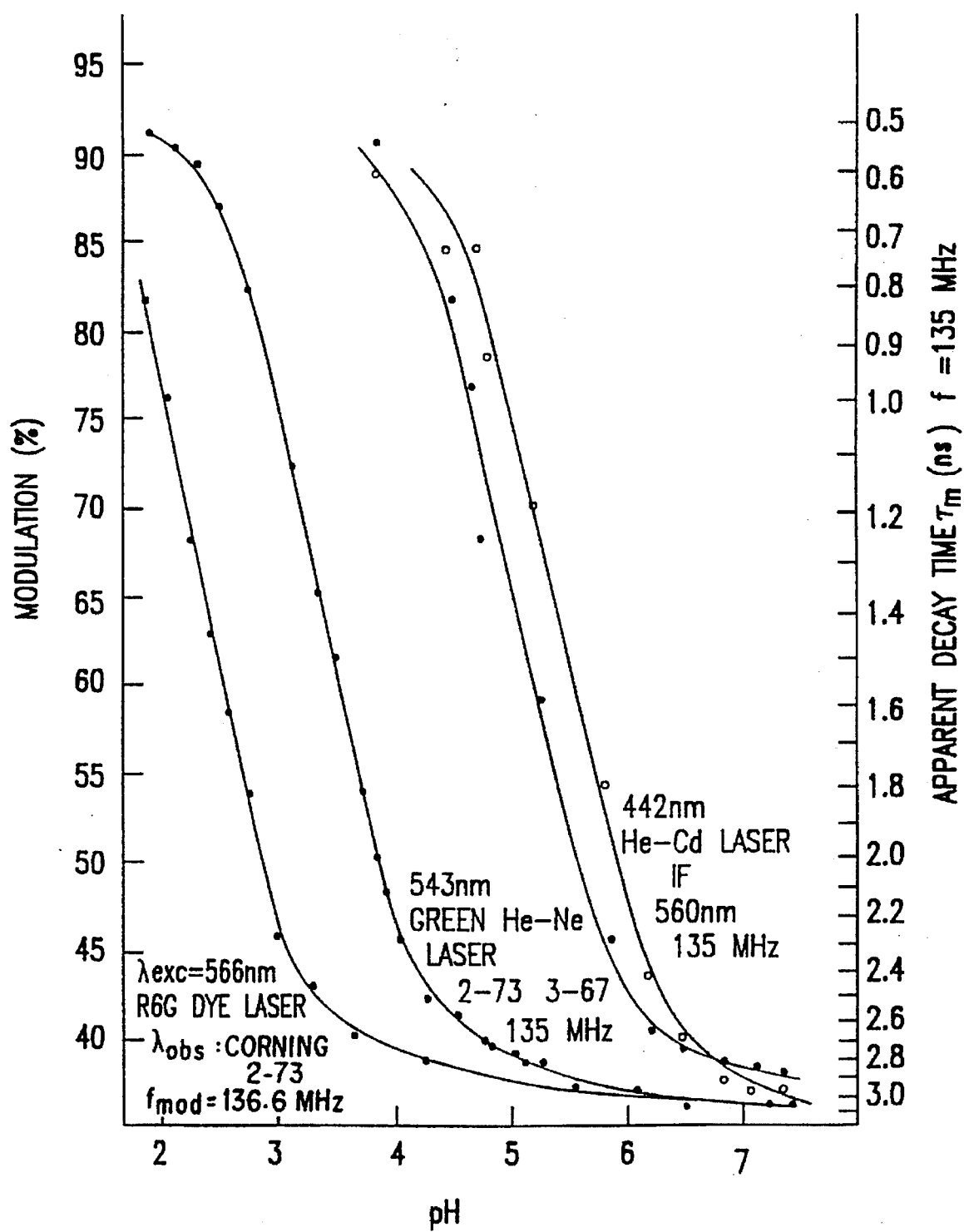
FIG. 9B is a modulation versus pH graph for the probe shown in FIG. 9A.

A sample containing the pH indicator Resorufin Sodium Salt was irradiated using a helium-cadmium laser having an excitation wavelength of 442 nm modulated at a modulation frequency of 135 MHz. Initially, a Corning 3-67 filter was used to filter the emission beam. As shown in FIGS. 9A and 9B, at pH=6.1, the measured phase shift with respect to the modulated excitation was 58.1 degrees, and the modulation of the emission was 41.1% of the modulation of the excitation. At an emission wavelength of 560 nm, the measured phase shift with respect to the modulated excitation was 41.1 degrees, and the modulation of the emission was 45.3% of the modulation of the excitation. At an excitation wavelength of 543 nm and a pH of 3.5, the measured phase shift with respect to the modulated excitation was 29.8 degrees, and the modulation of the emission was 62.6% of the modulation of the excitation. At an excitation wavelength of 566 nm and a pH of 2.67, the measured phase shift with respect to the modulated excitation was 39.5 degrees, and the modulation of the emission was 55.0% of the modulation of the excitation.

EXAMPLE 10

Figure 10:
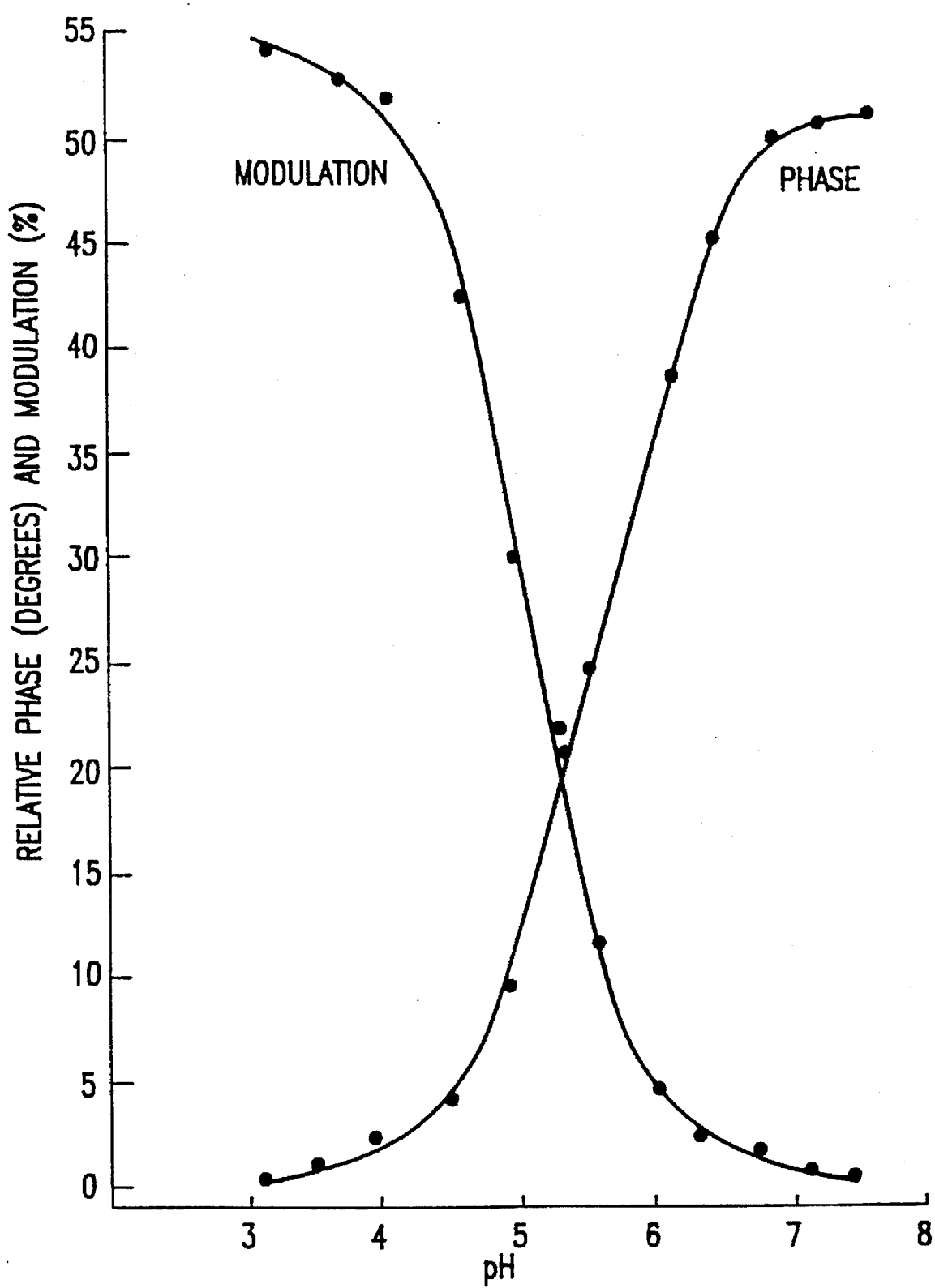
FIG. 10 is a phase/modulation versus pH graph for another of the probes, resorufin acetate, used in another preferred embodiment of the invention.

A sample containing the pH indicator Resorufin Acetate was irradiated using a helium-cadmium laser having an excitation wavelength of 442 nm modulated at a modulation frequency of 135 MHz. Initially, a Corning 3-67 filter was used to filter the emission beam. As shown in FIG. 10, at pH 5.52, the measured phase shift with respect to the modulated excitation was 41.0 degrees, and the modulation of the emission was 50.4% of the modulation of the excitation. In FIG. 10, the phase is depicted as relative to its value at pH=3.1 of 16.4 degrees with respect to the excitation. Similarly, the modulation is depicted relative to its value at pH=7.5 of 38.1%.

EXAMPLE 11

Figure 13A:
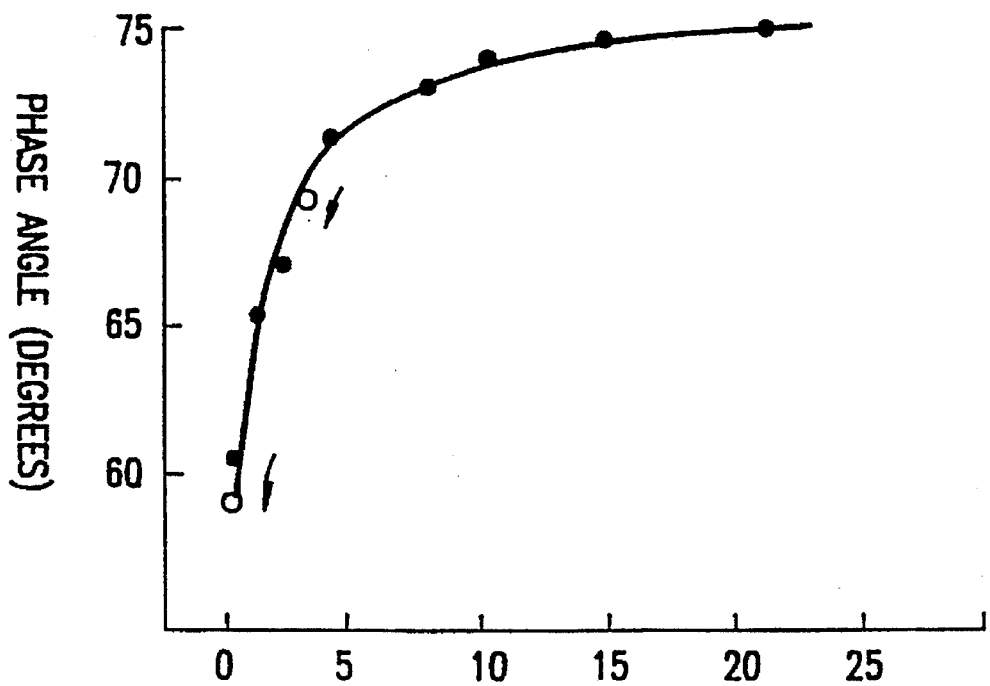
FIG. 13A is a phase versus concentration graph for carbon dioxide for the probe, carboxy SNARF-6, used in another preferred embodiment of the invention.
Figure 13B:
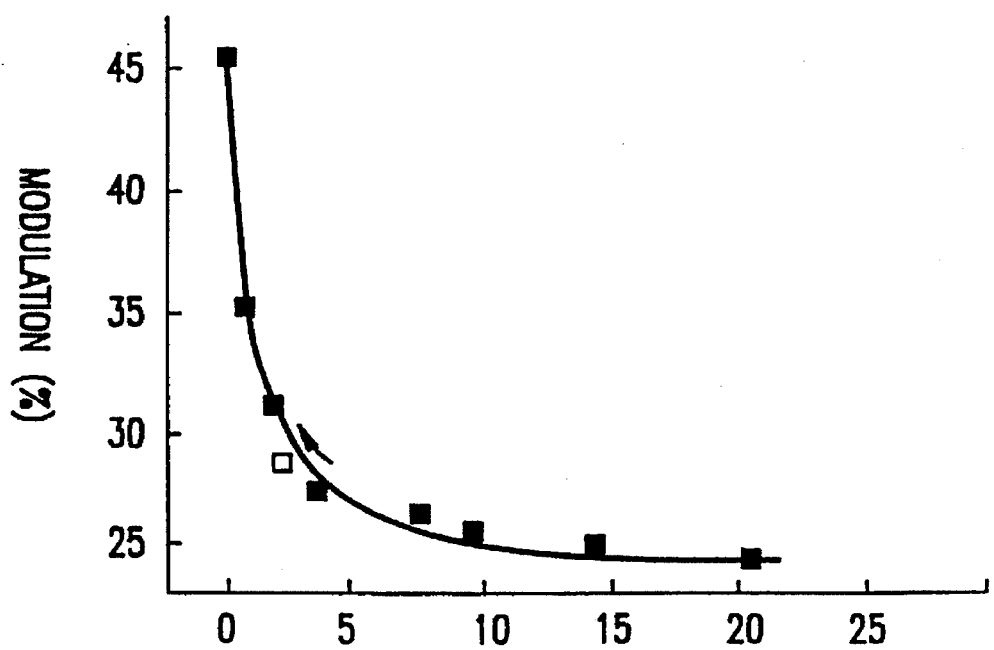
FIG. 13B is a modulation versus concentration graph corresponding to the graph shown in FIG. 13A.

A sample containing the indicator carboxy SNARF-6 in hydrogel was irradiated using a green helium-neon laser having an excitation wavelength of 543 nm modulated at a modulation frequency of 135 MHz. A Corning 2-73 filter was used to filter the emission. As shown in FIGS. 13A and 13B, at 4% carbon dioxide (expressed as a percentage of total gas molecules overlaying the sample, with the balance being nitrogen), the measured phase shift with respect to the modulated excitation was 71.1 degrees, and the modulation of the emission was 27.5% of the modulation of the excitation.

All of the probes in Examples 1–11 are excitable with a 543 nm green helium-neon laser, except for BCECF acid. The use of a green helium-neon laser is particularly advantageous in the clinical setting because the laser is inexpensive and reliable.

These probes also exhibit acceptable phase and modulation changes. The response for BCECF acid is the smallest, and the response for resorufin sodium salt is the largest. As discussed above, phase shifts on the order of 30–60 degrees are preferred. Accordingly, of the above pH probes, carboxy snafl-2 and carboxy snarf-6 exhibit the particularly useful phase and modulation changes.

The results are dependent on the excitation and emission wavelengths, since these variables cause either the bound or unbound form of the probe to be emphasized, as explained above. For pH measurements, this allows the range of pH sensitivity to be selected depending on the choice of excitation wavelength or emission wavelength.

Some of the above probes are more dependent on these variables than others. For example, of the seminaphthofluoresceins, carboxy-snafl-2 appears to be the best at allowing measurements of various pH ranges by changing the excitation and emission wavelengths. Of the seminaphthorhodafluors, carboxy snarf-6 appears to be the best in this respect. Although both of the resorufins show large changes in phase and modulation, resorufin sodium salt appears to allow greater range of pH sensitivity than resorufin acetate.

The method of the invention is particularly useful in a clinical setting for measuring blood gases quickly and effectively. For example, the pH of a blood sample can be measured and certain blood gases, such as carbon dioxide concentration, can be determined therefrom. This method of determining the pH and carbon dioxide concentration of a blood sample can be used in vitro or in vivo including, for example, blood gas catheters and other bedside patient monitors, and non-invasive blood gas measurements.

B. Measuring Calcium Ion Concentration

The method of the invention may also be used to measure the calcium ion concentration of a sample. To measure calcium ion concentration, certain tetraacetic acids, particularly Quin-2 (2-[(2-amino-5-methylphenoxy)methyl]-6-methoxy-8-amino-quinoline-N,N,N',N'-tetraacetic acid, tetrapotassium salt) having the following structure has proven particularly useful:

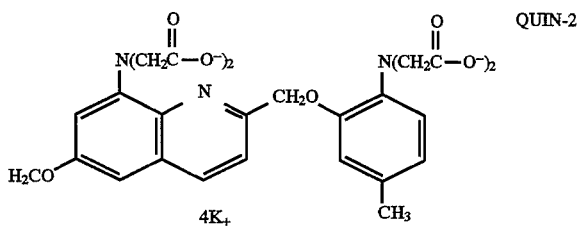

QUIN-2

Figure 11:
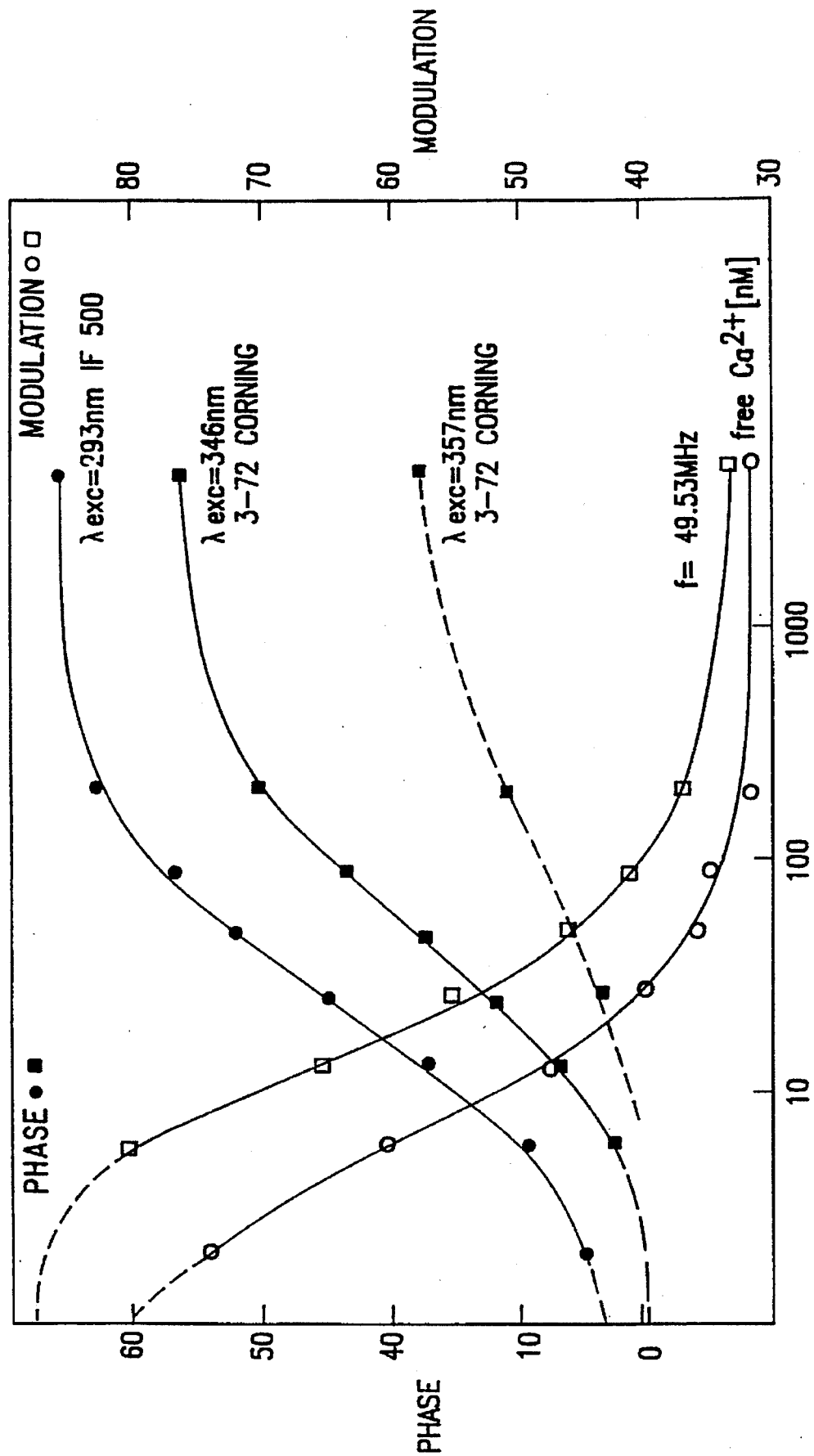
FIG. 11 is a phase/modulation versus calcium ion concentration graph for another of the probes, Quin-2, used in another preferred embodiment of the invention.

The short lifetime component shown in FIG. 11 corresponds to the probe bound to the calcium ions, and the long lifetime component corresponds to the free probe.

Another particularly useful probe in the measurement of calcium ion concentration is that known by the tradename Calcium Green.

EXAMPLE 12

A sample containing the calcium ion indicator Quin-2 in a buffered solution of 130 mM KCl dissolved in 10 mM MOPS and 1 mM EDTA at a pH of 7.06 was irradiated using a laser having an excitation wavelength of 293 nm modulated at a frequency of 49.53 MHz. The emission wavelength was 500 nm. As shown in FIG. 11, at a calcium ion concentration of 26 nM, the measured phase shift with respect to the modulated excitation was 45.1 degrees, and the modulation of the emission was 40.0% of the modulation of the excitation. At a calcium ion concentration of 26 nM and an excitation wavelength of 346 nm, the measured phase shift with respect to the modulated excitation was 32.0 degrees, and the modulation of the emission was 54.2% of the modulation of the excitation.

EXAMPLE 13

Figure 18:
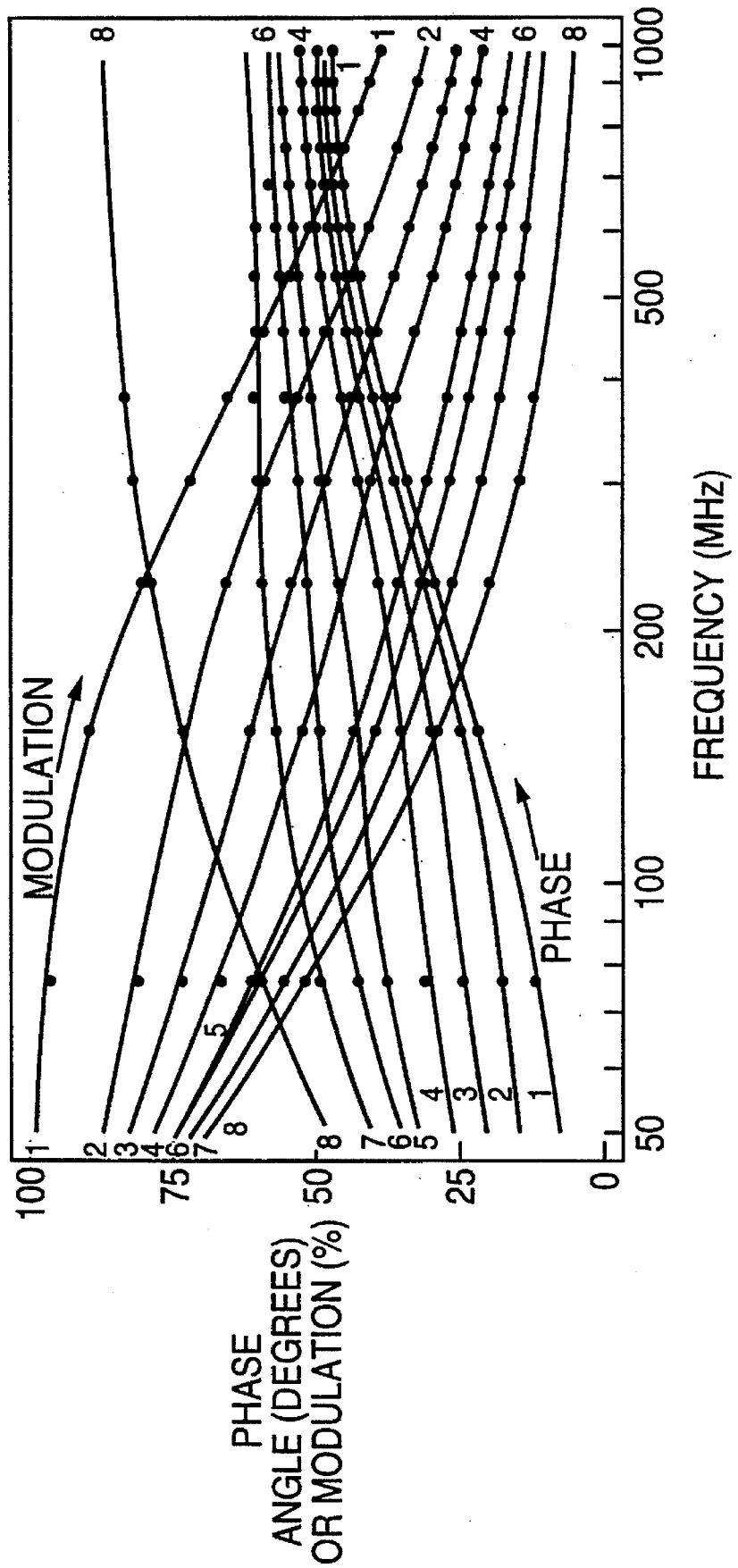
FIG. 18 is a phase/modulation versus frequency graph for the probe calcium green.

A sample containing the calcium ion indicator Calcium Green in a buffered solution of 130 mM KCl dissolved in 10 mM MOPS and 1 mM EDTA at a pH of 7.02 was irradiated using an ion argon laser having an excitation wavelength of 514.5 nm modulated at a frequency of 75.9 MHz. The emission was collected for wavelengths >515 nm using a 3-69 Corning filter. The following Tables 1–9 indicate phase angle and modulation of the emission as a % of modulation of the excitation over a wide range of $Ca^{2+}$ concentrations and modulation frequencies. These values are graphed in FIG. 18.

TABLE 1

$Ca^{2+}$ concentration: 0 nM

| f (MHz) | phase angle (degrees) | modulation of the emission as a % of modulation of the excitation |
|---|---|---|
| 75.9 | 12.1 | 96.0 |
| 151.8 | 21.3 | 88.7 |
| 227.7 | 29.0 | 79.9 |
| 303.6 | 36.2 | 71.4 |
| 379.5 | 37.7 | 64.6 |
| 455.4 | 40.3 | 58.2 |
| 531.3 | 42.5 | 53.9 |
| 607.2 | 43.8 | 50.0 |
| 683.1 | 44.5 | 46.6 |
| 759.0 | 45.6 | 44.0 |
| 834.9 | 46.3 | 41.5 |
| 910.8 | 46.4 | 39.4 |
| 986.7 | 47.0 | 37.4 |

TABLE 1-continued $Ca^{2+}$ concentration: 0 nM

| f (MHz) | phase angle (degrees) | modulation of the emission as a % of modulation of the excitation |
|---|---|---|
| 1062.6 | 48.0 | 36.0 |
| 1138.5 | 48.8 | 34.1 |
| 1290.3 | 48.5 | 31.4 |
| 1442.1 | 47.9 | 29.6 |
| 1745.7 | 48.3 | 26.4 |
| 2732.4 | 46.8 | 20.2 |

TABLE 2

$Ca^{2+}$ concentration: 7 nM

| f (MHz) | phase angle (degrees) | modulation of the emission as a % of modulation of the excitation |
|---|---|---|
| 75.9 | 17.7 | 80.6 |
| 151.8 | 24.7 | 72.5 |
| 227.7 | 31.4 | 65.2 |
| 303.6 | 36.5 | 58.2 |
| 379.5 | 39.8 | 52.4 |
| 455.4 | 48.2 | 47.4 |
| 531.3 | 44.0 | 43.2 |
| 607.2 | 45.1 | 40.0 |
| 683.1 | 45.6 | 37.8 |
| 759.0 | 46.2 | 35.6 |
| 834.9 | 46.8 | 34.0 |
| 910.8 | 48.3 | 32.0 |
| 1062.6 | 48.4 | 29.1 |
| 1214.4 | 49.0 | 26.2 |
| 1366.2 | 48.7 | 24.6 |
| 1518.0 | 48.2 | 23.5 |
| 1745.7 | 49.5 | 21.4 |
| 1973.4 | 48.1 | 19.9 |

TABLE 3

$Ca^{2+}$ concentration: 16 nM

| f (MHz) | phase angle (degrees) | modulation of the emission as a % of modulation of the excitation |
|---|---|---|
| 75.9 | 24.3 | 72.5 |
| 151.8 | 29.8 | 58.9 |
| 227.7 | 34.9 | 53.6 |
| 303.6 | 39.1 | 47.6 |
| 379.5 | 42.2 | 42.9 |
| 455.4 | 44.1 | 38.9 |
| 531.3 | 45.5 | 36.6 |
| 607.2 | 46.2 | 33.0 |
| 683.1 | 47.4 | 30.7 |
| 759.0 | 47.8 | 28.9 |
| 834.9 | 48.1 | 27.4 |
| 910.8 | 48.6 | 26.2 |
| 986.7 | 50.0 | 24.8 |
| 1062.6 | 50.7 | 23.7 |
| 1138.5 | 50.0 | 22.3 |
| 1290.3 | 50.0 | 20.5 |

TABLE 4

$Ca^{2+}$ concentration: 29 nM

| f (MHz) | phase angle (degrees) | modulation of the emission as a % of modulation of the excitation |
|---|---|---|
| 75.9 | 30.8 | 65.8 |
| 151.8 | 34.6 | 52.3 |
| 227.7 | 39.0 | 45.2 |

TABLE 4-continued

Ca²⁺ concentration: 29 nM

| f (MHz) | phase angle (degrees) | modulation of the emission as a % of modulation of the excitation |
|---|---|---|
| 303.6 | 42.4 | 40.0 |
| 379.5 | 44.9 | 35.6 |
| 455.4 | 47.0 | 32.2 |
| 531.3 | 48.5 | 29.2 |
| 607.2 | 49.6 | 27.2 |
| 683.1 | 50.2 | 25.4 |
| 759.0 | 50.9 | 23.6 |
| 834.9 | 51.1 | 22.5 |
| 910.8 | 52.2 | 21.4 |
| 986.7 | 52.0 | 20.6 |

TABLE 5

Ca²⁺ concentration: 54 nM

| f (MHz) | phase angle (degrees) | modulation of the emission as a % of modulation of the excitation |
|---|---|---|
| 75.9 | 37.5 | 60.5 |
| 151.8 | 42.7 | 43.1 |
| 227.7 | 45.6 | 35.5 |
| 303.6 | 48.6 | 30.8 |
| 379.5 | 49.9 | 27.0 |
| 455.4 | 51.6 | 24.2 |
| 531.3 | 52.1 | 21.9 |
| 607.2 | 52.8 | 20.2 |
| 683.1 | 53.6 | 18.8 |
| 759.0 | 54.4 | 17.6 |
| 834.9 | 55.2 | 16.6 |

TABLE 6

Ca²⁺ concentration: 101 nM

| f (MHz) | phase angle (degrees) | modulation of the emission as a % of modulation of the excitation |
|---|---|---|
| 75.9 | 42.3 | 57.9 |
| 151.8 | 48.3 | 38.6 |
| 227.7 | 51.5 | 30.6 |
| 303.6 | 52.9 | 25.6 |
| 379.5 | 54.3 | 22.2 |
| 455.4 | 55.4 | 18.7 |
| 531.3 | 55.8 | 17.6 |
| 607.2 | 56.6 | 16.4 |
| 683.1 | 57.6 | 22.2 |

TABLE 7

Ca²⁺ concentration: 238 nM

| f (MHz) | phase angle (degrees) | modulation of the emission as a % of modulation of the excitation |
|---|---|---|
| 75.9 | 48.9 | 54.9 |
| 151.8 | 56.5 | 34.3 |
| 227.7 | 59.5 | 25.8 |
| 303.6 | 59.7 | 21.0 |
| 379.5 | 60.5 | 18.1 |
| 455.4 | 59.6 | 16.1 |
| 531.3 | 59.7 | 14.4 |
| 607.2 | 60.3 | 13.0 |

TABLE 8

Ca²⁺ concentration: 447 nM

| f (MHz) | phase angle (degrees) | modulation of the emission as a % of modulation of the excitation |
|---|---|---|
| 75.9 | 50.4 | 53.5 |
| 151.8 | 59.4 | 32.4 |
| 227.7 | 62.4 | 23.8 |
| 303.6 | 63.2 | 19.4 |
| 379.5 | 63.5 | 16.3 |
| 455.4 | 63.9 | 14.2 |
| 531.3 | 64.3 | 12.7 |

TABLE 9

Ca²⁺ concentration: 500 nM

| f (MHz) | phase angle (degrees) | modulation of the emission as a % of modulation of the excitation |
|---|---|---|
| 75.9 | 51.9 | 53.9 |
| 151.8 | 61.3 | 32.3 |
| 227.7 | 64.8 | 23.4 |
| 303.6 | 66.3 | 18.5 |
| 379.5 | 66.6 | 15.6 |
| 455.4 | 66.5 | 13.3 |
| 531.3 | 66.5 | 11.8 |

As can be seen from the above, as was found in Examples 1–11, the results in Examples 12 and 13 are dependent on the excitation and emission wavelengths, since these variables cause either the bound or unbound form of the probes to be emphasized, as explained above. For calcium ion concentration measurements, this allows the range of calcium ion concentration sensitivity to be selected depending on the choice of excitation wavelength and/or emission wavelength.

It is also contemplated that the probes known under the tradenames Fura-2, Indo-1, Rhod-2, Fluo-3, Calcium Orange and Calcium Crimson may be suitable for making calcium ion concentration measurements using the method of the present invention.

Sensing the calcium ion concentration of a sample is particularly useful for flow cytometry and fluorescent lifetime imaging applications.

C. Measuring Potassium Ion Concentration

The method of the invention may also be used to measure the potassium ion concentration of a sample. To measure potassium ion concentration, the probe known as PBFI, having the following structure, has been found to be particularly useful:

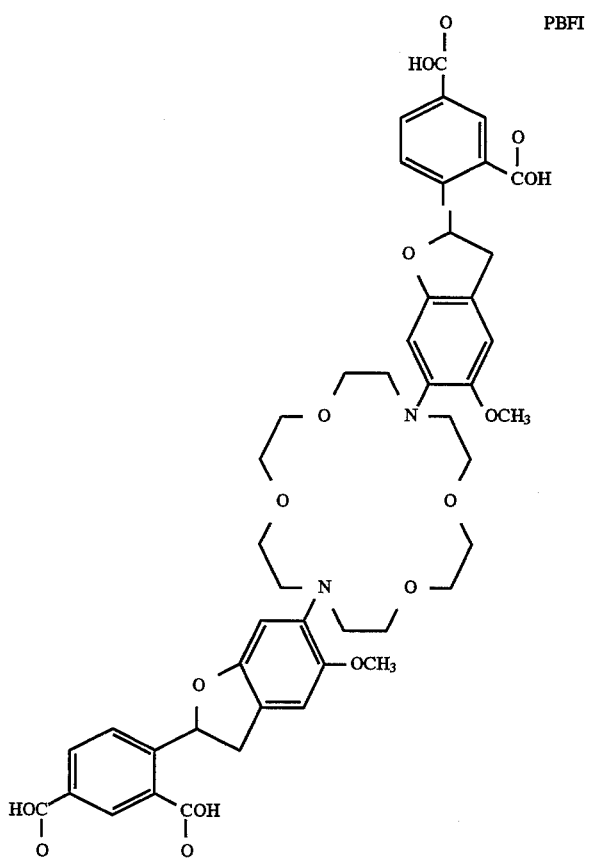

EXAMPLE 14

Figure 14:
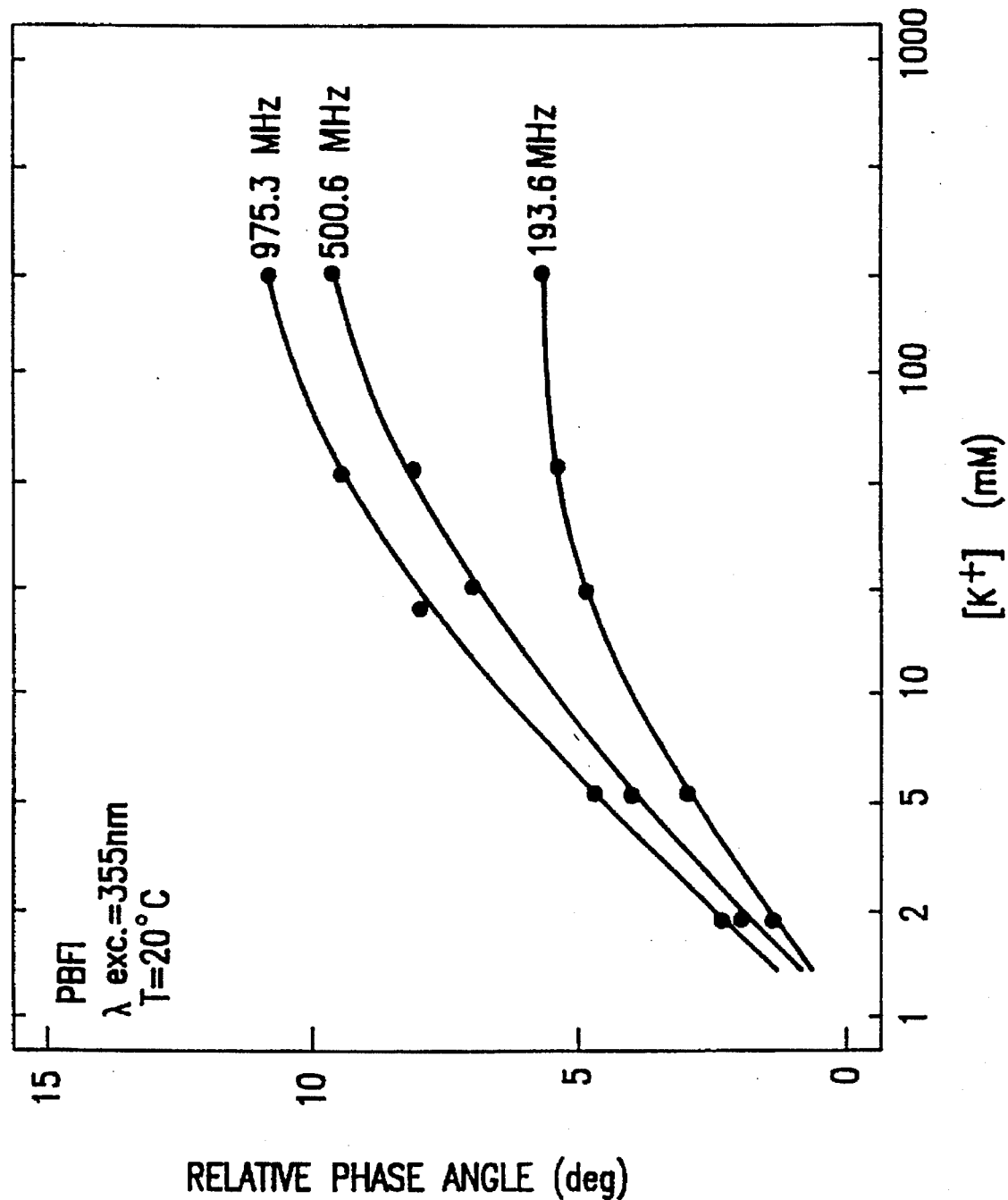
FIG. 14 is a phase versus concentration graph for potassium ion concentrations for another of the probes, PBFI, used in another preferred embodiment.

A sample containing the potassium ion indicator PBFI was irradiated using a laser having an excitation wavelength of 355 nm modulated at a frequency of 975.3 MHz. As shown in FIG. 14, at a potassium ion concentration of 200 mM, the measured phase shift with respect to the modulated excitation was 57.5 degrees. In FIG. 14, the phase is depicted as relative to its value at a potassium ion concentration of 0 mM of 48.1 degrees with respect to the excitation. At a modulation frequency of 193.6 MHz and a calcium ion concentration of 200 mM, the measured phase shift with respect to the modulated excitation was 31.2 degrees. The phase is depicted as relative to its value at a potassium ion concentration of 0 mM of 26.3 degrees with respect to the excitation.

The above is for illustrative purposes only. Modifications can be made within the scope of the invention as defined by the appended claims.

We claim:

1. A method of optically measuring analytes, said method comprising the steps of:

adding a photoluminescent ligand probe to a sample to be analyzed, said sample containing an analyte which is an ionic solute, wherein said probe is non-covalently bound to said ionic solute to form an analyte-bound probe species, and wherein bound and unbound species of said probe exist in said sample, said probe having intrinsic analyte-induced lifetime changes;

exciting the sample with radiation;

detecting the resulting emission beam from said bound and unbound species; and performing a calculation consisting essentially of calculating the apparent luminescence lifetime of the emission to determine the analyte concentration of the sample.

2. A method as in claim 1, wherein said probe is a fluorescent probe.

3. A method as in claim 1, wherein said method is used for the continuous in-vivo monitoring of blood gases.

4. A method as in claim 1, wherein the lifetime is calculated using phase-modulation fluorometry.

5. A method as in claim 1, further comprising the step of changing the apparent concentration sensitivity range of the probe by changing the wavelength of the modulated excitation and/or the wavelength of the emission.

6. A method as in claim 1, wherein the lifetime is calculated using time-resolved fluorometry.

7. A method as in claim 1, wherein the sample is excited using a green helium-neon laser.

8. The method of claim 1, wherein the analyte is the hydronium ion, potassium or calcium.

9. A method as in claim 1, wherein the sample is human blood or a fraction thereof.

10. A method as in claim 9, wherein said probe is selected from the group consisting of seminaphthorhodafluors, seminaphthofluoresceins and resorufins.

11. A method as in claim 1, wherein the sample is excited using a laser diode.

12. A method as in claim 11, wherein the laser diode is intrinsically modulated.

13. A method as in claim 1, wherein the analyte is hydronium ions.

14. A method as in claim 13, wherein said probe is selected from the group consisting of seminaphthorhodafluors, seminaphthofluoresceins and resorufins.

15. A method as in claim 13, wherein said probe is selected from the group consisting of the following formulae:

SEMINAPHTHORHODAFLUORS

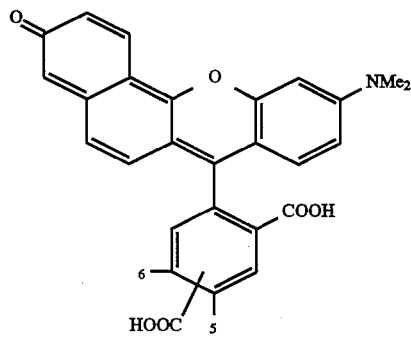

carboxy SNARF-1

19
-continued

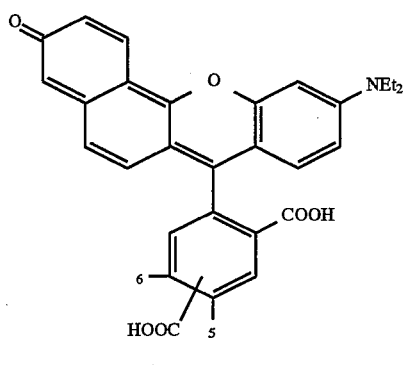

carboxy SNARF-2

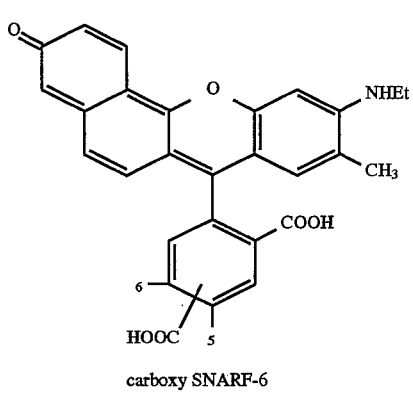

carboxy SNARF-6

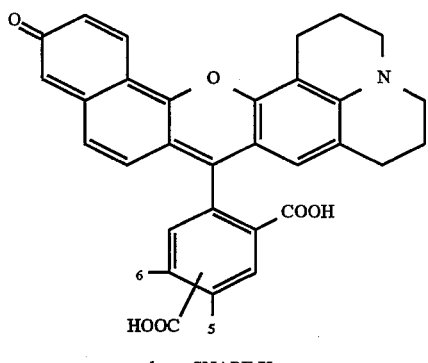

carboxy SNARF-X

SEMINAPHTHOFLUORESCEINS

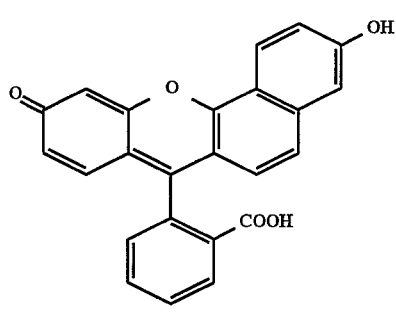

SNAFL-1

20
-continued

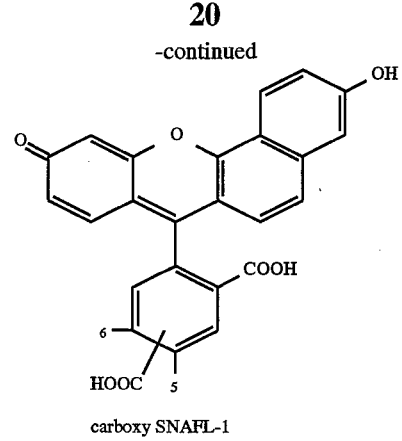

carboxy SNAFL-1

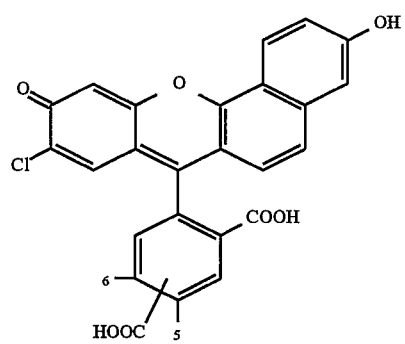

carboxy SNAFL-2

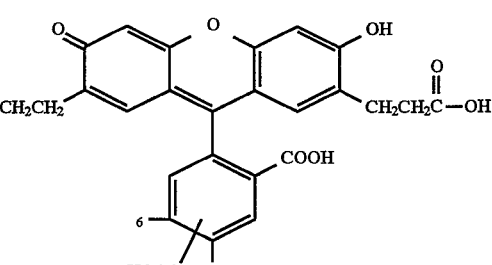

BCECF acid

RESORUFINS

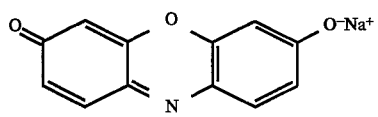

Resorufin sodium salt

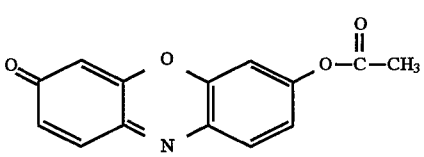

Resorufin acetate

16. A method as in claim 13, further comprising the step of calculating carbon dioxide concentration from the hydronium ion concentration.

17. A method as in claim 16, wherein the carbon dioxide concentration is calculated through the bicarbonate couple to pH.

18. A method of optically measuring analytes, said method comprising the steps of:

adding a photoluminescent ligand probe to a sample to be analyzed, said sample containing an analyte which is an ionic solute, wherein said probe is non-covalently bound to said ionic solute to form an analyte-bound probe species, and wherein bound and unbound species of said probe exist in said sample, said probe having intrinsic analyte-induced lifetime changes;

exciting the sample with radiation;

detecting the resulting emission beam from said bound and unbound species; and performing a calculation utilizing the apparent luminescence lifetime of the emission to determine the analyte concentration of the sample without utilizing fluorescence intensity in said calculation to determine the analyte concentration.

* * * * *